(12) United States Patent
Manson et al.

(10) Patent No.: US 11,857,225 B2
(45) Date of Patent: Jan. 2, 2024

(54) MULTIPLE SET SCREW INSERTION INSTRUMENT AND METHODS

(71) Applicant: Medos International Sarl, Le Locle (CH)

(72) Inventors: Alec Manson, Boston, MA (US); Richard Fournier, New Bedford, MA (US); Cory Emil, Milton, MA (US); Eric Biester, Barrington, RI (US); William Miller, Middleboro, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 0 days.

(21) Appl. No.: 17/522,177

(22) Filed: Nov. 9, 2021

(65) Prior Publication Data

US 2022/0142684 A1 May 12, 2022

Related U.S. Application Data

(60) Provisional application No. 63/111,610, filed on Nov. 9, 2020.

(51) Int. Cl.
*A61B 17/70* (2006.01)
*A61B 17/86* (2006.01)

(52) U.S. Cl.
CPC ...... *A61B 17/7091* (2013.01); *A61B 17/7035* (2013.01); *A61B 17/7076* (2013.01)

(58) Field of Classification Search
CPC ............ A61B 17/7091; A61B 17/7082; A61B 17/7076; A61B 17/865; A61B 17/8875–8894; A61B 2017/00371; A61B 2017/00407; B25B 23/04; B25B 23/06; B25B 23/065
See application file for complete search history.

(56) References Cited

U.S. PATENT DOCUMENTS 2,412,275 A * 12/1946 Klopovic .............. B25B 23/065
                                                       81/125
2,611,289 A *  9/1952 Frank ................... B25B 23/065
                                                       81/125

(Continued)

OTHER PUBLICATIONS

International Search Report and Written Opinion for Application No. PCT/EP2021/081169 dated May 4, 2022 (17 pages).

(Continued)

*Primary Examiner* — Jan Christopher L Merene
*Assistant Examiner* — Anna V. Little
(74) *Attorney, Agent, or Firm* — Barnes & Thornburg LLP

(57) ABSTRACT

This disclosure relates generally to surgical instruments used to deliver locking or set screws to secure a rod or spinal fixation element relative to an implanted bone anchor or other spinal fixation construct during spine surgery. In one embodiment, the inserter instrument can include an inner driver shaft, a ratcheted outer sleeve, and a handle configured to receive the shafts therein. The inner driver shaft can receive a plurality of set screws on a distal end thereof. A side latch, pawl, or button can engage with the ratcheted outer sleeve to facilitate step-wise advancement of the sleeve relative to the driver shaft for set screw delivery. Step-wise advancement can be controlled using another button that causes movement of the side latch.

14 Claims, 29 Drawing Sheets

(56) References Cited

U.S. PATENT DOCUMENTS

| | | | |
|---|---|---|---|
| 2,868,053 A * | 1/1959 | Jorgensen | B25B 23/065 411/932 |
| 5,640,889 A * | 6/1997 | Anderson | B25B 23/108 81/125 |
| 6,634,261 B1 * | 10/2003 | Griffin | B25B 23/065 81/125 |
| 7,717,921 B2 | 5/2010 | Rezach | |
| 7,722,623 B2 | 5/2010 | Franks et al. | |
| 7,846,167 B2 | 12/2010 | Garcia et al. | |
| 8,087,142 B2 | 1/2012 | Levin et al. | |
| 8,105,328 B2 | 1/2012 | Protopsaltis | |
| 8,403,933 B2 | 3/2013 | Rutledge | |
| 8,998,958 B2 | 4/2015 | Dauster et al. | |
| 9,675,353 B2 | 6/2017 | Ranucci et al. | |
| 10,258,450 B2 | 4/2019 | Criscuolo et al. | |
| 10,327,862 B2 | 6/2019 | Lubinski | |
| 10,426,527 B2 | 10/2019 | Doose et al. | |
| 10,548,642 B2 | 2/2020 | Harper | |
| 10,624,639 B2 | 4/2020 | Ranucci et al. | |
| 2005/0119667 A1 | 6/2005 | LePort et al. | |
| 2007/0088363 A1 * | 4/2007 | Rezach | A61B 17/8872 606/99 |
| 2007/0276403 A1 * | 11/2007 | Franks | A61B 17/7091 606/104 |
| 2008/0243190 A1 * | 10/2008 | Dziedzic | A61B 17/7091 606/264 |
| 2008/0255576 A1 * | 10/2008 | Protopsaltis | A61B 17/7091 227/176.1 |
| 2009/0211411 A1 * | 8/2009 | Guile | B25B 23/08 81/441 |
| 2011/0295282 A1 | 12/2011 | Glick et al. | |
| 2013/0296888 A1 * | 11/2013 | Harper | A61B 17/8875 606/139 |
| 2016/0374737 A1 * | 12/2016 | Bootwala | A61B 17/708 606/279 |
| 2019/0380748 A1 * | 12/2019 | Doose | A61B 17/7082 |

OTHER PUBLICATIONS

International Preliminary Report on Patentability for Application No. PCT/EP2021/081169 dated May 8, 2023 (12 pages).

* cited by examiner

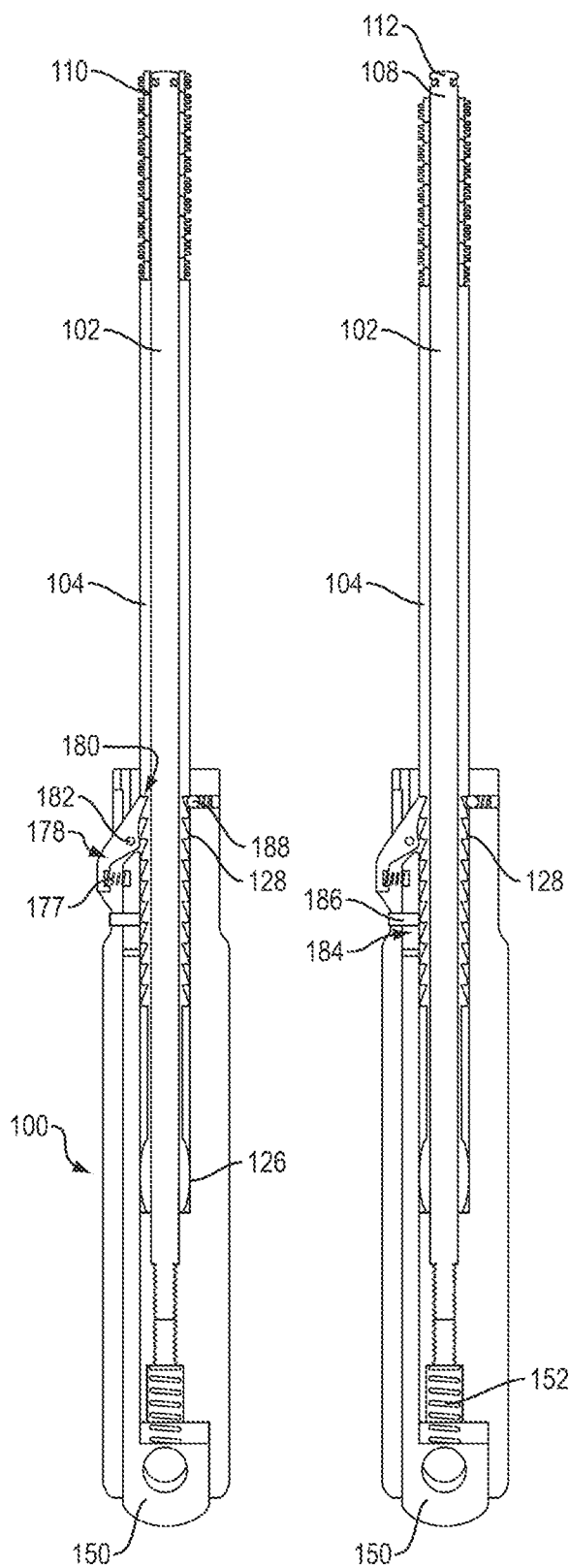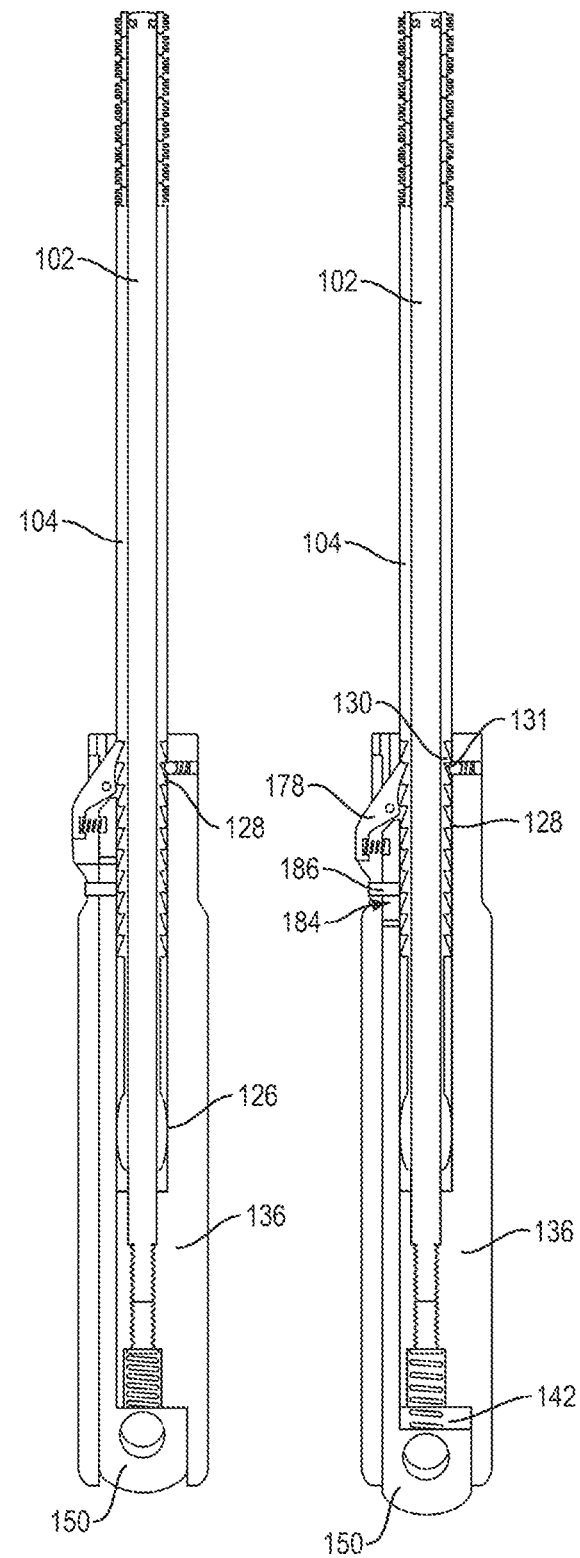
FIG. 13    FIG. 14    FIG. 15    FIG. 16

BALL DETENT IN
FIRST POSTION.

BALL DETENT IN NEXT POSTION
AFTER ONE BUTTON CLICK TO
ADVANCE TO THE NEXT SET SCREW.

MULTIPLE SET SCREW INSERTION INSTRUMENT AND METHODS

CROSS-REFERENCE TO RELATED APPLICATIONS

This application claims the benefit of U.S. Provisional Application No. 63/111,610, entitled "Multiple Set Screw Inserter," filed on Nov. 9, 2020. The entire contents of this application are hereby incorporated by reference in their entirety.

FIELD

This disclosure relates generally to surgical instruments and methods of use and, more particularly, to surgical instruments utilized to deliver locking or set screws to secure a rod or spinal fixation element relative to an implanted bone anchor or other spinal fixation construct during spine surgery.

BACKGROUND

During spine surgery, such as procedures to correct deformities in the spine, fixation constructs are often assembled to hold the spine in a desired shape. Such constructs often include a plurality of implanted bone anchors along multiple vertebrae and a connecting spinal fixation element, such as a rod, that is received within a head of each of the bone anchors and secured using a set screw. In many cases, the bone anchors are first implanted in the vertebrae, a rod is then positioned relative to the bone anchor heads, and set screws applied to secure the rod relative to each bone anchor.

Current posterior fixation systems that utilize the above-described implanted bone anchors and spinal fixation rods or elements coupled to the anchors require the delivery of set screws to each implanted anchor to secure the rod relative to the anchor. For each set screw/implanted anchor, a user must connect a set screw to an insertion instrument and deliver this assembly to the implanted bone anchor, often through narrow extension tubes, guides, or other instrumentation that extends from the implanted bone anchor away from the patient's body and toward the user performing the surgery. Further, in many cases a first user, such as an assistant, loads the set screw on the insertion device and passes this assembly to a second user, such as a surgeon, who introduces the assembly into the patient's body and delivers the set screw. The second user then returns the insertion device to the first user for reloading and the process repeats for each implanted bone anchor—of which there may be several, especially in spinal deformity correction procedures where especially long spinal fixation constructs may be assembled. This process requires some amount of operative time, which can become significant. Each pass also adds complexity and risk to the procedure that a component might be mishandled, dropped, etc.

Accordingly, there is a need for improved instruments and methods for delivering set screws, including improved instruments and methods for delivering multiple set screws to secure components to bone anchors during spine surgery while minimizing loading time of the instrument.

SUMMARY

The present disclosure generally relates to multiple set screw insertion instruments and methods of use that address challenges of prior approaches. The multiple set screw insertion instruments disclosed herein can reduce the number of passes of instruments between a surgeon and assistant while maintaining the ability to deliver set screws to affix spine surgery instrumentation. Generally speaking, the multiple set screw insertion instruments disclosed herein can include an inner driver shaft having a plurality of set screws stacked thereon, and an outer driver sleeve having a ratcheting portion for stepwise advancement of set screws along the inner driver shaft for insertion into bone anchors and other spinal instrumentation. The inner driver shaft and the outer sleeve can be received within a handle having a button for actuating the instrument. Actuation of the instrument can result in relative movement between the inner driver shaft and the outer sleeve to sequentially eject set screws from the instrument into a bone anchor receiver head or other spinal instrumentation.

In one aspect, a surgical instrument is provided that can include a shaft with a distal portion configured to drive a set screw and seat a plurality of set screws stacked against one another on the shaft, as well as a handle coupled to the shaft, a sleeve disposed over the shaft and configured to contact a proximal-most set screw stacked on the shaft, a first button disposed in the handle and configured to advance the sleeve distally relative to the shaft by a first increment, and a second button disposed in the handle and configured to permit retraction of the sleeve proximally.

Any of a variety of alternative or additional features can be included and are considered within the scope of the present disclosure. For example, in some embodiments, the sleeve can include a plurality of ratchet teeth. In certain embodiments, the first increment can correspond to a distance between two adjacent teeth of the plurality of ratchet teeth. In some embodiments, the instrument can further include a detent disposed in the handle that is configured to interface with the plurality of ratchet teeth to resist movement of the sleeve. The detent can be a spring-biased ball in certain embodiments. In some embodiments, the second button can be biased to contact a ratchet tooth of the plurality of ratchet teeth. And in certain embodiments, the second button can permit proximal retraction of the sleeve when the bias of the second button is overcome.

In some embodiments, the instrument can further include a spring clip disposed around a distal end of the shaft and configured to retain a set screw thereon by interference fit.

In certain embodiments, movement of the first button can cause movement of the second button. In some embodiments, movement of the first button can translate the second button distally. Further, in some embodiments the first button can be biased proximally such that proximal movement of the first button moves the second button proximally relative to the sleeve.

In some embodiments, an outer diameter of the plurality of set screws stacked on the shaft can be substantially equal to an outer diameter of the sleeve disposed over the shaft.

In certain embodiments, the sleeve can also include a retention mechanism thereon for preventing ejection of the sleeve from the handle. The retention mechanism can abut the second button to retain the sleeve within the handle in certain configurations.

In some embodiments, the first button can be disposed on a proximal end of the handle and the second button can be disposed on a side of the handle.

In certain embodiments, any of the first button and the second button can be biased In another aspect, a surgical method is provided that can include delivering a first set screw to a first implanted bone anchor using an inserter, actuating the inserter to advance a second set screw distally relative to a shaft of the inserter, and delivering a second set screw to a second implanted bone anchor using the inserter.

As with the instruments described above, the methods disclosed herein can include any of a variety of additional or alternative steps that are considered within the scope of the present disclosure. In some embodiments, for example, actuating the inserter can include depressing a first button disposed in a handle of the inserter. Further, in some embodiments actuating the inserter can include advancing a sleeve disposed over the shaft distally to urge the second set screw toward a distal end of the shaft.

In another aspect, a surgical method is provided that can include actuating a first button disposed in a handle of an inserter, sliding a sleeve disposed over a shaft of the inserter proximally, and advancing a plurality of set screws proximally over a distal portion of the shaft of the inserter.

In some embodiments, the first button can be disposed in a side of the handle. And in certain embodiments, the sleeve can slide to abut a proximal wall of a recess formed in the handle.

Any of the features or variations described herein can be applied to any particular aspect or embodiment of the present disclosure in a number of different combinations. The absence of explicit recitation of any particular combination is due solely to avoiding unnecessary length or repetition.

BRIEF DESCRIPTION OF THE DRAWINGS

The aspects and embodiments of the present disclosure can be more fully understood from the following detailed description taken in conjunction with the accompanying drawings, in which:

FIG. 13 is a cross-sectional side view of the multiple set screw insertion instrument of FIG. 1 in the first position;

FIG. 14 is a cross-sectional side view of the multiple set screw insertion instrument of FIG. 1 following set screw insertion;

FIG. 15 is a cross-sectional side view of the multiple set screw insertion instrument of FIG. 1 in the second position with a button depressed;

FIG. 16 is a cross-sectional side view of the multiple set screw insertion instrument of FIG. 1 in a third position that is reset for set screw insertion;

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. The devices, systems, and methods specifically described herein and illustrated in the accompanying drawings are non-limiting embodiments. The features illustrated or described in connection with one embodiment may be combined with the features of other embodiments. Such modifications and variations are intended to be included within the scope of the present disclosure. Additionally, to the extent that linear, circular, or other dimensions are used in the description of the disclosed devices and methods, such dimensions are not intended to limit the types of shapes that can be used in conjunction with such devices and methods. Equivalents to such dimensions can be determined for different geometric shapes, etc. Further, like-numbered components of the embodiments can generally have similar features. Still further, sizes and shapes of the devices, and the components thereof, can depend at least on the anatomy of the subject in which the devices will be used, the size and shape of objects with which the devices will be used, and the methods and procedures in which the devices will be used.

The present disclosure generally relates to multiple set screw insertion instruments and methods of use that address challenges of prior approaches. The multiple set screw insertion instrument disclosed herein can reduce the number of passes of instruments between a surgeon and assistant while maintaining the ability to deliver set screws to affix spine surgery instrumentation. In one embodiment, the multiple set screw insertion instrument can include an inner driver shaft having a plurality of set screws stacked thereon, and an outer driver sleeve having a ratcheting portion for stepwise advancement of set screws along the inner driver shaft for insertion into bone anchors and other spinal instrumentation. The inner driver shaft and the outer sleeve can be received within a handle having a button for actuating the instrument. Actuation of the instrument can result in relative movement between the inner driver shaft and the outer sleeve to sequentially eject set screws from the instrument into a bone anchor receiver head or other spinal instrumentation.

Figure 1:
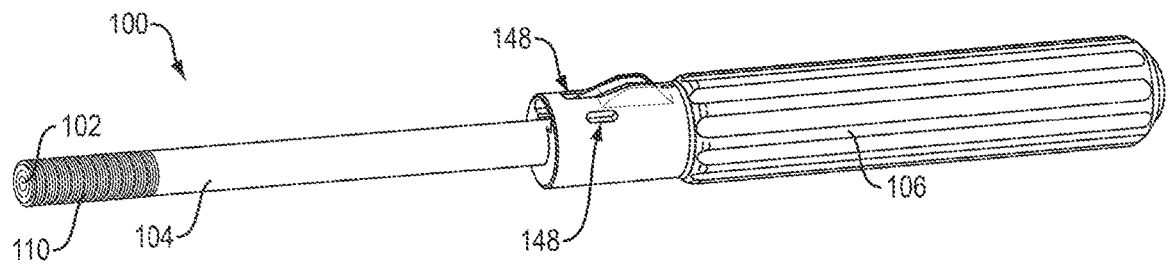
FIG. 1 is a perspective view of one embodiment of a multiple set screw insertion instrument of the present disclosure having a plurality of set screws disposed thereon.
Figure 2A:
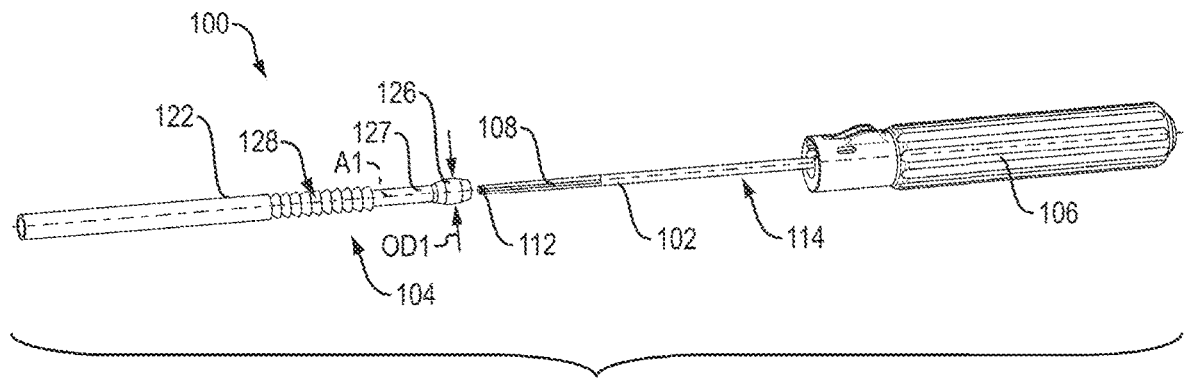
FIG. 2A is an exploded perspective view of the multiple set screw insertion instrument of FIG. 1.
Figure 2B:
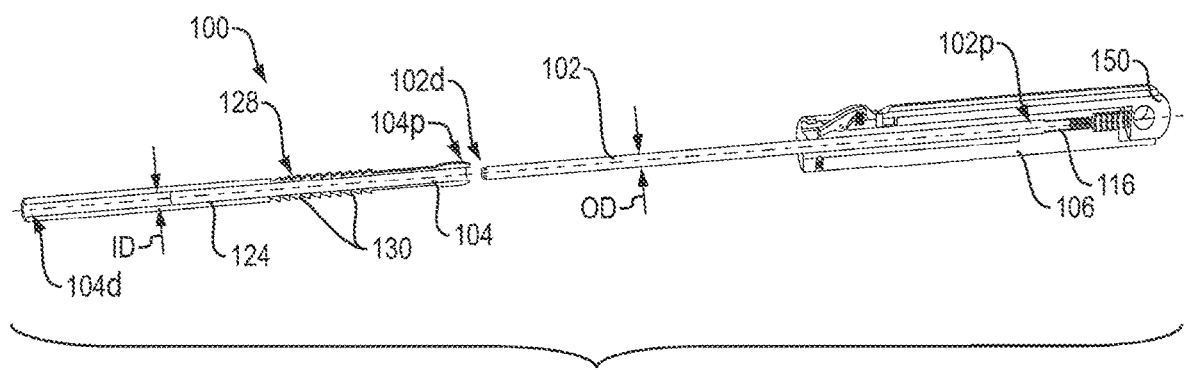
FIG. 2B is a cross-sectional perspective view of the multiple set screw insertion instrument of FIG. 2A.

FIGS. 1-2B illustrate one embodiment of a multiple set screw insertion instrument or inserter instrument 100. The multiple set screw insertion instrument 100 can be used to deliver set screws to spinal instrumentation during procedures, e.g., spinal surgery. The instrument 100 can include an inner driver shaft 102, an outer sleeve 104, and a handle 106 configured to receive the inner driver shaft 102 and the outer sleeve 104 therein. The inner driver shaft 102 can include a drive feature 108 for receiving a plurality of set screws 110 thereon. In some embodiments, the instrument 100 can include a central longitudinal axis A1 extending therethrough such that the axis A1 passes through one or more of the inner driver shaft 102, the outer sleeve 104, and/or the handle 106. In use, the inner driver shaft 102 can be received inside the outer sleeve 104, with the outer sleeve being configured to translate relative to the inner driver shaft 102. Translation of the outer sleeve 104 can sequentially advance a set screw 110 of the plurality of set screws 110 to a distal tip 112 located on the drive feature 108 of the inner driver shaft 108 after ejection of a previous set screw from the instrument, e.g., due to insertion of the previous set screw into spinal implementation.

Figure 4:
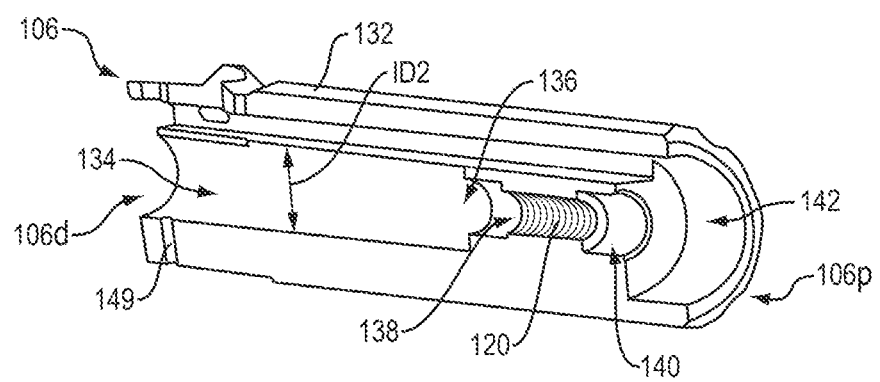
FIG. 4 is a cross-sectional perspective view of a handle of the multiple set screw insertion instrument of FIG. 1.

FIGS. 2A-2B in particular illustrate assembly of the multiple set screw insertion instrument 100. The inner driver shaft 102 can include a generally tubular body 114 having a proximal end 102p and a distal end 102d with the central longitudinal axis A1 extending therebetween. The tubular body 114 can be solid, though in some embodiments, the body can be hollow such that an opening extends therethrough. The proximal end 102p of the inner driver shaft 102 can include a mating feature 116, e.g., a threaded male member, as shown in FIG. 2B, for coupling with a corresponding threaded bore 120 in the handle 106, as described in greater detail below with regard to FIG. 4. In some embodiments, the mating feature 116 can be keyed to be received within the bore in a specific orientation such that the inner driver shaft 102 couples to the handle 106 in a specific orientation.

Figure 3:
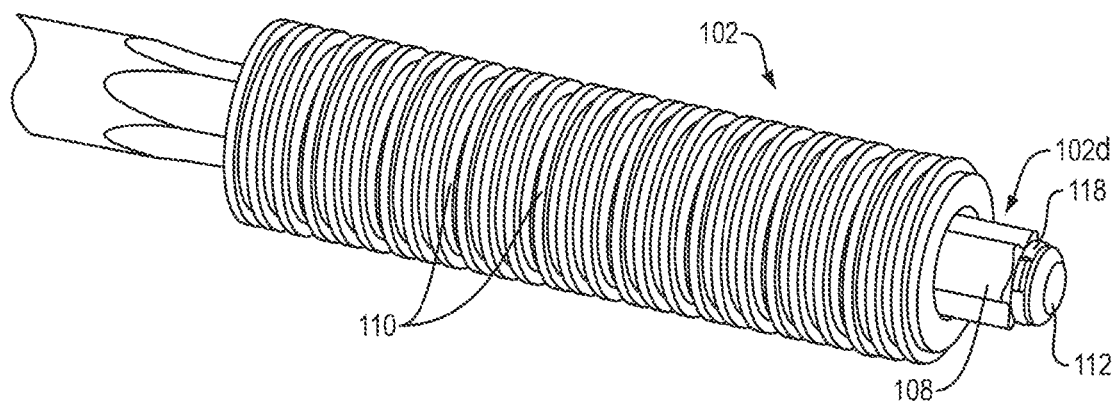
FIG. 3 is a perspective view of an inner driver shaft of the multiple set screw insertion instrument of FIG. 1 having the plurality of set screws disposed thereon.

The drive feature 108 at the distal end 102d of the inner drive shaft 102 can be shaped to correspond to an inner opening in the plurality of set screws 110. As shown, the drive feature 108 can be a male Torx®-shaped protrusion extending along a distal portion of the shaft 102 such that a plurality of set screws 110 can be stacked on the drive feature 108. The plurality of set screws 110 can include a recess shaped to correspond to the drive feature 108 to allow the set screws to be secured to the drive feature and rotated therewith while also allowing for proximal translation of the set screws over the drive feature 108. In some embodiments, the drive feature 108 can include a retention feature 118, as shown in FIG. 3, to prevent unintended separation of the set screws 110 from the drive feature 108. Further details of the retention feature are discussed in greater detail below.

The overall profile of the inserter instrument 100 can be similar to an elongate set screw driver. The outer sleeve 104 can include a generally tubular body 122 having proximal and distal ends 104p, 104d defining a channel 124 therebetween. The channel 124 can extend in a common axis of the central longitudinal axis A1 of the inner driver shaft 102 such that the central longitudinal axis A1 extends from the proximal end 104p to the distal end 104d of the outer shaft 104. As shown, the channel 124 can be configured to receive at least a portion of the inner driver shaft 104 therethrough. For example, the body 122 of the outer sleeve 104 can define an inner diameter ID that is substantially the same size or larger than an outer diameter OD of the inner driver shaft 102 to receive the inner driver shaft 102 therethrough.

In some embodiments, the outer sleeve 104 can include a non-uniform outer diameter OD1. For example, the outer diameter OD1 of the tubular body 122 of the outer sleeve 104 can be larger in some locations than at others. In some embodiments, the outer diameter OD1 can taper along a length thereof. In some embodiments, the outer sleeve 104 can taper from the proximal end 104p of towards the distal end 104d such that the proximal end 104p engages one or more features within the handle 106 to selectively permit or prevent translation of the outer sleeve 104 relative to the handle and/or the inner driver shaft 102. As shown, the outer sleeve 104 can include a proximal head 126 thereon having a larger outer diameter OD1 than a portion of the sleeve extending distally from the proximal head. The proximal head 126 can function as a retention mechanism that prevents inadvertent or undesired separation of the sleeve 104 from the handle 106. For example, the proximal head 126 can interface with the latch or button 178 to provide a stop against complete removal of the sleeve 104 from the handle 106. The stop can prevent axial translation of the outer shaft 104 with respect to the other components of the inserter instrument 100. While a proximal head 126 is shown, the stop can include a ribbed surface, a protrusion, a catch, or another component configured to retain the outer sleeve 104 within the handle 106.

The outer sleeve 104 can include a ratchet portion 128 formed along the tubular body 122. As shown, the ratchet portion 128 can extend along an intermediate section of the outer sleeve 104, though in some embodiments, the ratchet portion 128 can extend along any length of the sleeve. The ratchet portion 128 can include a series of ratchet teeth, ribs, or protrusions 130 that are formed along the outer surface of the outer sleeve 104. The ratchet portion 128 can engage with one or more components of the instrument 100, such as the pawl 178 discussed below, for step-wise advancement of the outer shaft 104 with respect to other components, as discussed in greater detail below. The ratchet portion 128 can extend around a circumference of the tubular body 122 to allow the outer sleeve 104 to be inserted into the handle 106 in any rotational orientation. In use, the ratchet portion 128 can allow the outer sleeve 104 to provide a hard stop behind a set screw, which can aid a user in starting to thread the set screw into the implant and prevent proximal movement of the set screw or outer sleeve if a user exerts axial pushing forces on the device during insertion. In addition, the ratchet portion 128 can facilitate the advancement of a next set screw toward a distal end of the driver shaft 102 in connection with insertion of a prior set screw into a spinal fixation construct, such as a bone screw receiver member.

The handle 106 can include a tubular body 132 having a central lumen 134 formed therein. The central lumen 134 can extend from a distal end 106d of the handle 106 to the proximal end 106p along the central longitudinal axis A1 of the instrument 100 to receive one or more of the inner driver shaft 102 and/or the outer sleeve 104 therethrough. The central lumen can include an inner diameter ID2 that can be substantially the same as or larger than an outer diameter OD1 of the outer sleeve 104 to allow the outer sleeve to be disposed within the central lumen 134.

The central lumen 134 can include a receiving portion 136 at the proximal end 106p of the handle 106. The receiving portion 136 can extend within the central lumen 134 to receive the proximal end 102p of the inner driver shaft 102 therein. As shown in greater detail in FIG. 4, the receiving portion 136 can include a bore 138 having a reduced diameter portion that lies along the central longitudinal axis A1 with the central lumen 134. In some embodiments, the receiving portion 136, or a section of thereof, can be threaded. For example, as discussed above, the receiving portion 136 can include threads 120 thereon to allow threading of the inner driver shaft 102 thereto. During assembly, the proximal end 102p of the inner driver shaft 102 can be inserted into the receiving portion 136 with the mating feature 116 threaded into the threads 120 to couple the inner driver shaft 102 to the handle 106.

The receiving portion 136 can include a lumen 140 formed therein. For example, the threads 120 can extend through the receiving portion 136 and terminate at, or proximate to, the lumen 140. The lumen 140 can receive one or more coupling features of the instrument 100 therein, as described in greater detail below. The handle 106 can include a recess 142 formed at a proximal end 106p thereof. For example, as shown, the receiving portion 136 can terminate distal to the proximal end 106p of the handle 106 to define the recess 142 therebetween. The recess 142 can receive one or more components that are configured to actuate the instrument. For example, as shown, a button 150 can be disposed within the handle 106 to control advancement of the outer sleeve 104 to urge the set screws 110 distally.

The handle 106 can be made from a variety of materials, including any of a variety of plastics, ceramics, or metals, among others. In some embodiments, the handle 106 can include over-moldings of multiple materials, such as a silicone over-molding formed on another underlying material. The handle 106 can include a series of openings 148 at the distal end 106d thereof to allow for components of the instrument 100 to facilitate operation thereof. The series of openings 148 can extend transversely into the central lumen 134 to be in communication with the outer sleeve 104 disposed therein. The series of openings 148 are discussed in greater detail with respect to FIGS. 11 and 12 below.

Figure 5:
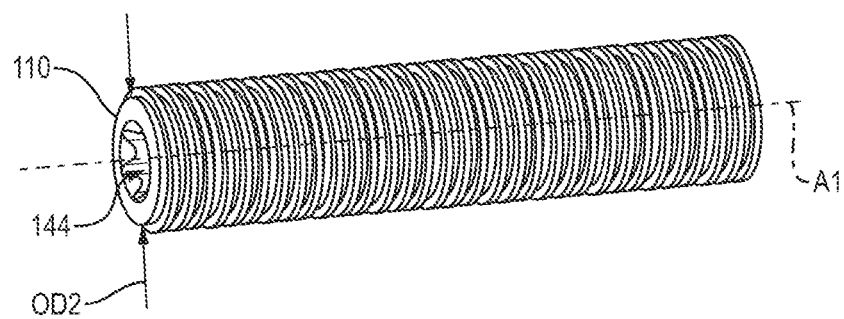
FIG. 5 is a perspective view of the plurality of set screws used with the multiple set screw insertion instrument of FIG. 1.

FIG. 5 illustrates a plurality of set screws 110 that can used with the multiple set screw insertion instrument 100 of the present disclosure. As shown, each set screw in the plurality of set screws 100 can include a female drive feature or through-bore 144 cut completely therethrough. The set screws 110 can be stacked on top of one another such that an axis A passing therethrough aligns with the central longitudinal axis A1. The female drive feature 144 can be configured to receive the male drive feature 108 of the inner driver shaft 102 therethrough to dispose the stack of set screws 110 along the inner driver shaft. For example, the through-bore 144 can include a geometry complementary to the drive feature 108 to allow the set screw 110 to stack onto the inserter shaft 102 and be rotationally driven by the inserter shaft 102 when the inserter instrument 100 is rotated. The through-bore 144 can be sized to allow for axial translation of each of the set screws 110 along the drive feature 108 when the outer sleeve 104 is advanced relative to the inner driver shaft 102. Moreover, each set screw can have an outer diameter OD2 and the profile of the outer sleeve 104 can, in some embodiments, be no larger than the outer diameter OD2 of the set screws 100.

Figure 6:
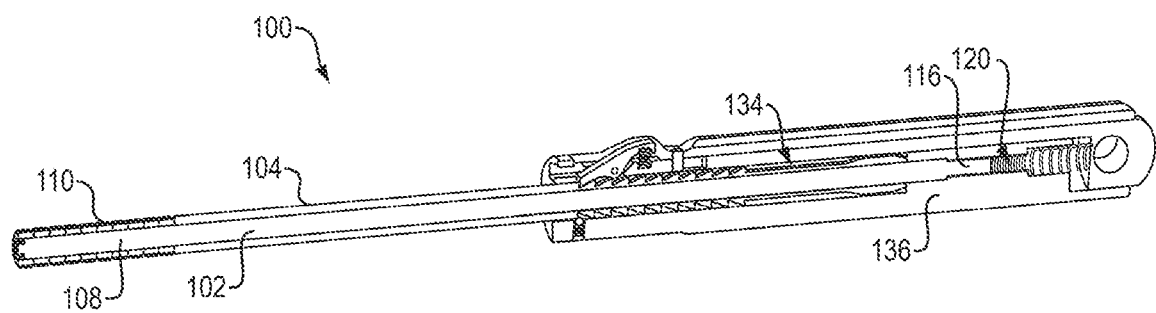
FIG. 6 is a cross-sectional perspective view of the multiple set screw insertion instrument of FIG. 1 in a first position.
Figure 7:
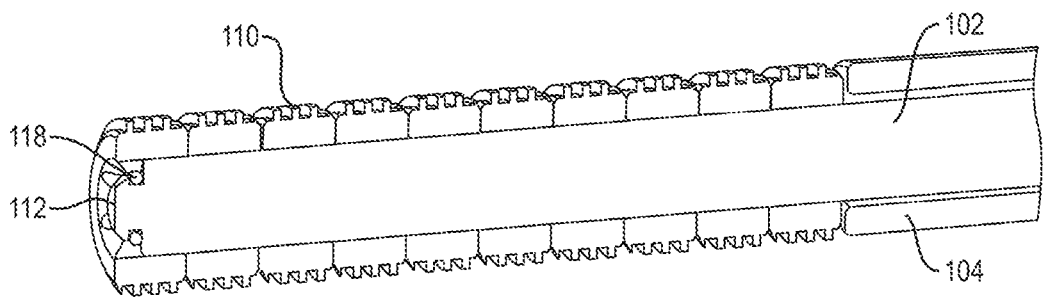
FIG. 7 is a cross-sectional detail view of the distal end of the multiple set screw insertion instrument of FIG. 1.
Figure 8:
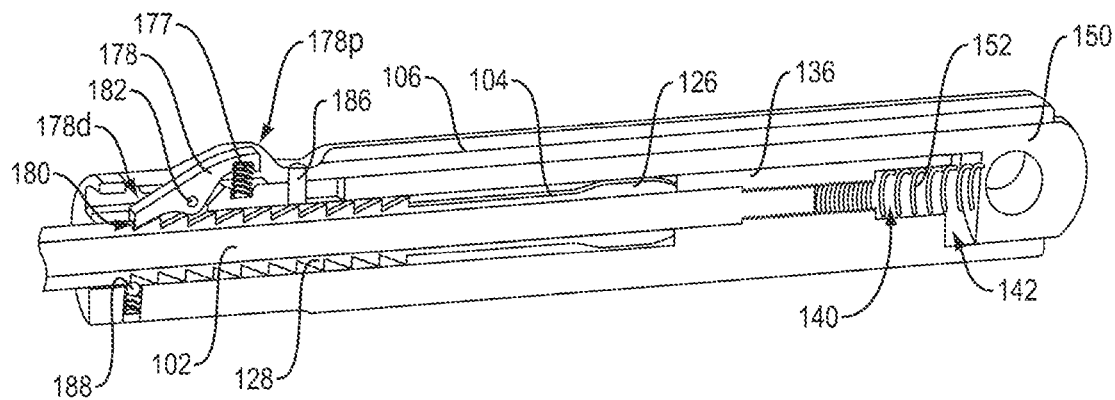
FIG. 8 is a cross-sectional detail view of the handle of the multiple set screw insertion instrument of FIG. 1.

FIGS. 6-8 illustrate the inserter instrument in greater detail. As shown, the inserter instrument 100, when placed in an initial position, includes the inner driver shaft 102 disposed within the channel 124 of the outer sleeve 104, with both components received within the central lumen 134 of the handle 106. Specifically, as noted above, the mating feature 116 of the inner driver shaft 102 can be threaded into the threads 120 within the receiving portion 136, while the proximal end 104p of the outer sleeve 104 can abut the receiving portion 136. The plurality of set screws 110 can be disposed on the drive feature 108 of the inner driver shaft 102 distal to the outer sleeve 104.

FIG. 7 illustrates a relationship between the stack of set screws 110 and the inner driver shaft 102 in greater detail. As noted above, the inner driver shaft 102 can include a retention feature 118, e.g., a spring clip or a circlip, which engages a distal tip 112 of the drive feature 108. As shown in FIG. 7, the spring clip 118 disposed at the distal end of the drive feature 108 can provide an interference fit between the spring clip and set screw 110, thereby limiting unwanted distal translation between the set screws and the drive feature.

FIG. 8 illustrates the interaction of the inner driver shaft 102, the outer sleeve 104, and the handle 106 of the inserter instrument 100 while in the initial position described above. The outer shaft 104 is received within the central lumen 134 while the proximal head 126 abuts the receiving portion 136. The bore 140 can receive a biasing element 152, such as a coil spring, that is configured to compress and extend in an axial direction when engaged with one or more components of the instrument 100. For example, as shown, the biasing element 152 can be disposed between the receiving portion 136 and the button 150. The biasing element 152 can bias the button 150 proximally such that the button 150 at least partially extends out of the recess 142.

Figure 9:
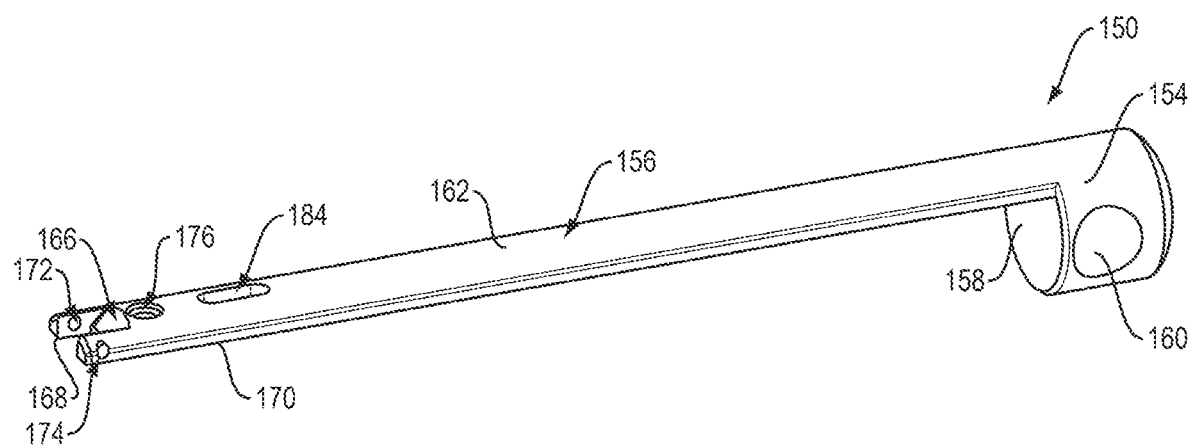
FIG. 9 is a perspective view of a button of the multiple set screw insertion instrument of FIG. 1.
Figure 10:
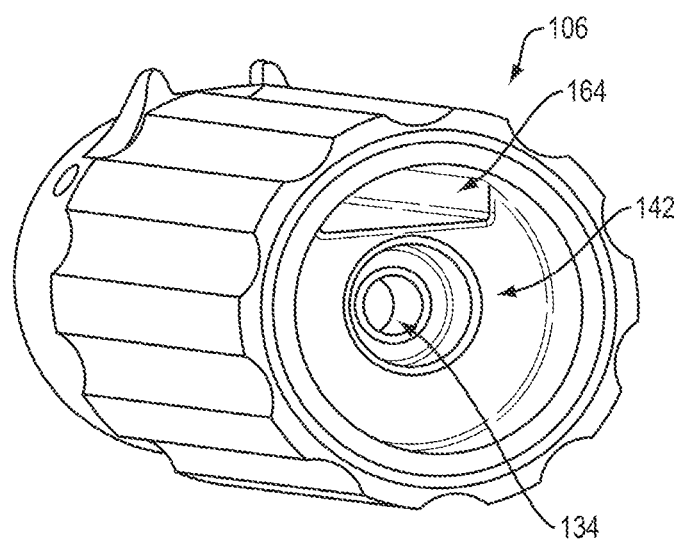
FIG. 10 is a perspective view of the proximal end of the handle of the multiple set screw insertion instrument of FIG. 1.

FIG. 9 illustrates the button 150 in greater detail. As shown, the button 150 includes a proximal head 154 and a distal body 156 extending therefrom. The proximal head 154 can include an outer diameter (not shown) that is substantially the same or smaller than a diameter of the recess 142 to allow the head to be disposed within the recess 142. The head 154 can include a distal-facing surface 158 for engaging a portion of the biasing element 152 to compress the biasing element when the button 150 is actuated. In some embodiments, the proximal head 154 can include a bore 160 formed therein.

The distal body 156 can include a sidewall 162 that extends from the proximal head 154 and runs along an interior portion of the inserter instrument handle 106. For example, the handle 106 can include a lumen 164 formed therein to allow the distal body 156 to pass therethrough. The lumen 164 can, in some embodiments, be separate from the central lumen 134. As shown in FIG. 8, the lumen 164 can terminate within an interior of the handle 106, e.g., distal to the receiving portion 136. In some embodiments, however, the second lumen 164 can extend through a distal end of the handle 106.

The distal body 156 can include one or more access points in the sidewall 162 thereof. The access points can align with one or more of the openings 148 in the handle 106 to facilitate advancement or indexing of the outer sleeve 104 relative to the handle. For example, the distal body 156 can include a cutout 166 formed therein that forms a pair of flanges 168, 170. The cutout 166 can align with one or more of the series of openings 148 in the handle 106, as noted above, to allow another component to extend through the handle 106 and the distal body 156 simultaneously and engage the outer sleeve 104, as discussed further below. As shown, one or more transverse openings 172, 174 can be formed in each of the flanges 168, 170 to facilitate coupling between components disposed within the cutout 166.

Access points can be formed in an outer surface of the sidewall 162. For example, the illustrated top surface of the sidewall 162 in FIG. 9 can include a recess 176 for receiving a biasing element 177, such as a coil spring or other biasing element. The biasing element 177 can, for example, bias another component disposed in the cutout 166 such that a portion thereof extends into the central lumen 134 to engage the outer shaft 104, as described in more detail below. One embodiment of such a component can be a pawl, latch, or button 178 (see FIG. 8) that extends into the central lumen 134 to engage the outer shaft 104. For example, the feature 178 can extend from a distal end 178d to a proximal end 178p, with the distal end 178d having an engagement surface 180 thereon. The engagement surface 180 can extend radially inward from the cutout 166 of the button 150 and the opening 148 of the handle 106 to engage the ratchet portion 128 of the outer sleeve 104. The pawl 178 can be coupled to the button 150 by a pin 182 received in the openings 172, 174 of the flanges 168, 170. The pin 182 can allow the pawl 178 to pivot about an axis of the pin 182. The proximal end 178p of the pawl 178 can include a recess to receive one end of the biasing element 177. The biasing element 177 can thereby urge the proximal end of the pawl 178p radially outward and the distal end of the pawl 178d radially inward toward the outer sleeve 104 and ratchet portion 128.

The sidewall 162 can include a slot 184 configured to receive a pin 186. The pin can be anchored within a bore formed in the sidewall of the handle 106 such that the pin does not translate axially relative to the handle. The slot can extend axially along the distal body 156 to allow axial translation of the button 150 between a proximal position and a distal position as defined by a length of the slot 184. Motion of the slot 184 relative to the pin 186 can define limits of translation of the distal body 156 and button 150 during actuation of the inserter instrument 100. For example, actuation of the button 150 can advance the distal body 156 until the pin 186 reaches a proximal end of the slot 184. Retraction of the button 150 can likewise move the pin 186 to the distal end of the slot 184, and interference between the pin and the end of the slot can prevent further movement of the button 150.

The inserter instrument 100 can also include a detent 188, such as a spring plunger or ball detent, received through an opening 149 in the handle 106. The detent 188, which is illustrated as a ball bearing biased radially inward by a coil spring, can engage the ratchet portion 128 to resist movement of the outer sleeve 104 relative to the handle 106. This can prevent undesired proximal or distal movement of the outer sleeve 104 relative to the handle 106, and can be particularly useful in preventing proximal movement of the outer sleeve 104 with the button 150 when the button retracts proximally after actuation. It will be appreciated that, in some embodiments, a leaf spring, a cantilevered deformable element, or other component can be used in place of the illustrated spring plunger of the instrument 100.

Figure 11:
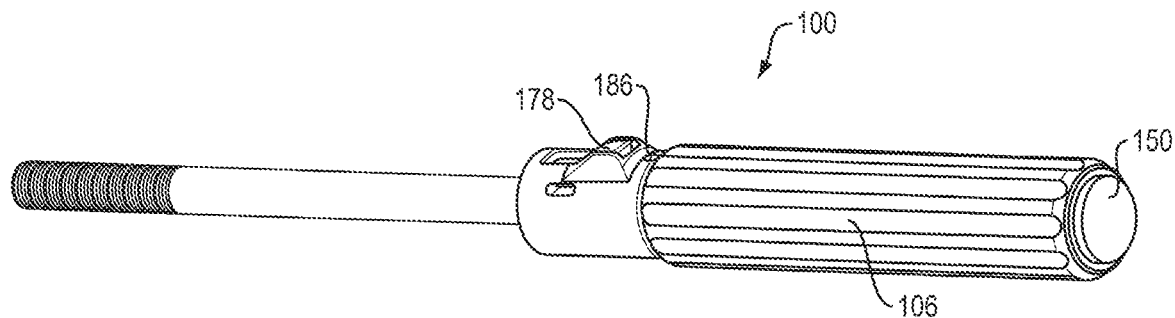
FIG. 11 is a perspective view of the multiple set screw insertion instrument of FIG. 1 in the first position.
Figure 12:
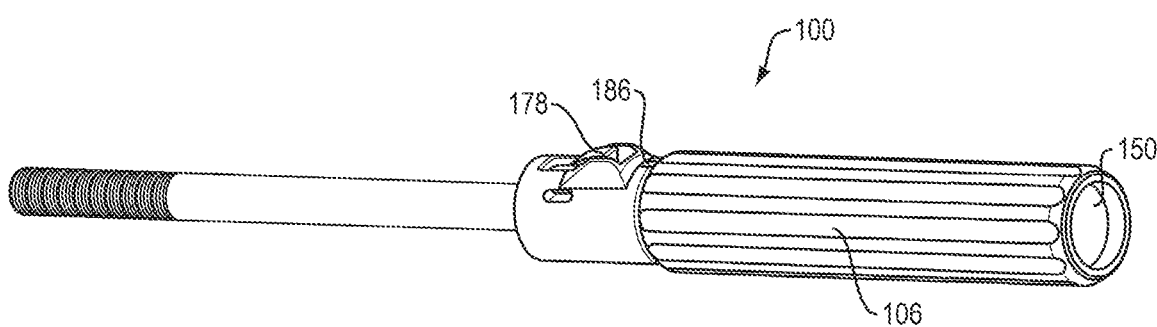
FIG. 12 is a perspective view of the multiple set screw insertion instrument of FIG. 1 in a second position with a button depressed.

FIGS. 11-16 illustrate actuation of the multiple set screw insertion instrument 100 in greater detail. As shown in FIG. 11, the button 150 of the multiple set screw insertion instrument 100 can, in an initial position, protrude proximally from the proximal end of the handle 106. Once actuated, as shown in FIG. 12, the resistance of the biasing element 152 can be overcome and the button 150 can move distally into the recess 142 of the handle 106.

FIGS. 13-16 illustrate a sequence of use of the multiple set screw insertion instrument 100 to insert a set screw during a procedure. Similar to FIG. 11, FIG. 13 shows the multiple set screw insertion instrument 100 in an initial position with a plurality of set screws 110 stacked onto a distal portion of the inner driver shaft 102. In this configuration, the first button 150 is biased to a proximal-most position and the pawl or second button 178 is biased to a position where its distal end engagement surface 180 is received within a distal-most recess 130 of the ratchet portion 128 of the outer sleeve 104. The outer sleeve 104 is prevented from proximal movement relative to the driver shaft 102 and handle 106 by interaction between the proximal end of the outer sleeve and the handle receiving portion 136, as well as by the interaction of the ratchet portion 128 with the pawl 178, which is in turn limited by interaction of the pin 186 and the slot 184. Accordingly, a user can urge a distal-most set screw to be placed into, e.g., a receiving member of a bone anchor to couple the set screw thereto. Axial and rotational forces can be transferred to the distal-most set screw to facilitate insertion thereof. Once the set screw 110 is coupled to the bone anchor, the multiple set screw insertion instrument 100 can be withdrawn proximally such that the distal-most set screw overcomes any resistive force from a retention feature 118 and comes off the driver shaft 102. Alternatively or in addition, a user can depress the button 150 to advance the outer sleeve 104 relative to the driver shaft 102, as described below, to aid in ejecting the distal-most set screw from the device.

As shown in FIG. 14, the drive feature 108 and the distal tip 112 of the inner driver shaft 102 can be exposed once the set screw is coupled to the bone anchor and the instrument is withdrawn proximally to decouple the distal-most set screw from the instrument. To advance the stack of set screws 110 distally towards the tip 112, the button 150 can be actuated, as shown in FIG. 15. Actuation of the button 150 can overcome the force of the biasing element 152 and distal advancement of the button 150 includes advancement of the distal body 156 within the lumen 164 relative to the handle 106. Advancement of the distal body 156 includes advancement of the pawl 178. The pawl 178, which is engaged with the distal-most recess 130 of the ratchet portion 128, urges the outer sleeve 104 distally along with the pawl and button 150. The actuation of the button can also provide sufficient force to overcome the resistance of the detent 188 against movement of the outer sleeve 104.

Distal advancement of the outer sleeve 104 terminates when the pin 186 abuts the proximal end of the slot 174 and the distal-facing surface 158 of the button 150 reaches the proximal end of the recess 142. In such a position, the new distal-most set screw can be positioned proximate to the distal tip 112 of the driver shaft 108. In this orientation, as shown in FIG. 15, the detent 188 can engage a second recess 131 of the ratchet portion 128 to again provide a resistive force against movement of the outer sleeve 104. The button 150 can then be released and the biasing element 152 can return the button 150 to its proximal-most position. This can, in turn, urge the pawl 178 proximally. The resistance provided by the detent 188 can overcome the friction force between the pawl 178 and the ratchet portion 128 of the outer sleeve 104 such that the outer sleeve remains stationary relative to the handle 106 and the pawl 178 rides into the second recess 131 of the ratchet portion 128 as it moves proximally relative to the handle 106 and the outer sleeve 104. In the absence of the detent 188, the outer sleeve 104 could retract proximally with the pawl or button 178 due to the friction force between them. Once the button 150 returns to its proximal, initial orientation, the set screw insertion process can be repeated until the stack of set screws 110 along the inner driver shaft 102 have all been inserted into their desired locations and ejected from the insertion instrument.

Figure 17:
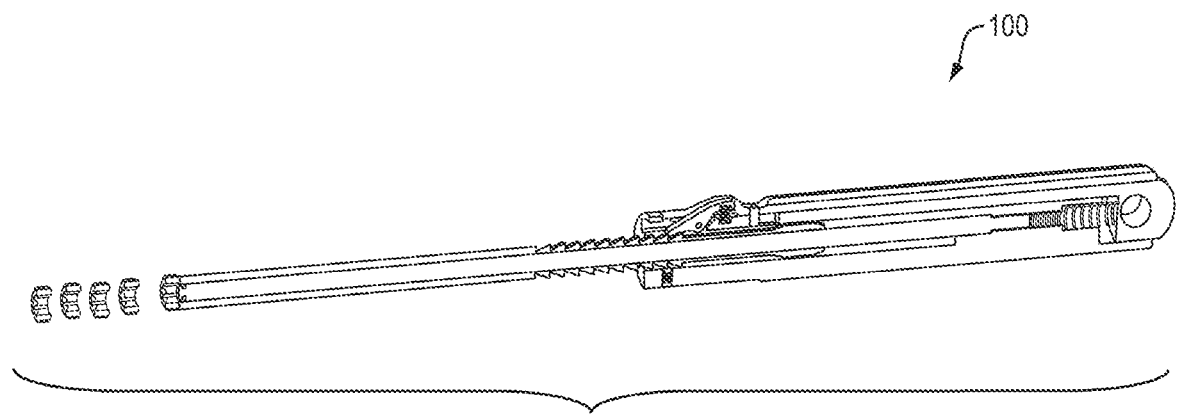
FIG. 17 is a cross-sectional perspective view of the multiple set screw insertion instrument of FIG. 1 with a final set screw disposed thereon.
Figure 18:
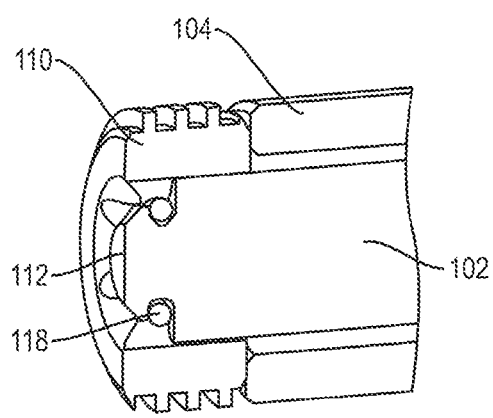
FIG. 18 is a cross-sectional detail view of the distal end of the multiple set screw insertion instrument of FIG. 17.

FIG. 17 illustrates the inserter instrument 100 following insertion of several set screws 110, such that a single set screw remains disposed thereon. As shown, the pawl or second button 178 and the detent 188 are engaged with a proximal-most recess of the ratchet portion 128 of the outer sleeve 104. FIG. 18 illustrates a detail view of the distal tip of the instrument 100, where the set screw is engaged with the retention feature 118 to prevent dislodgement of the set screw therefrom. The retention feature 118 can include a spring clip or circlip that surrounds the distal tip 112 and provides a radially-outward interference fit with the female drive recess or bore formed in the set screw 110. The spring clip 118 can be deformed to reduce its outer diameter, thereby allowing the application of sufficient force from the outer sleeve 104 to urge the set screw 110 over the clip and eject it from the instrument 100.

Figure 19A:
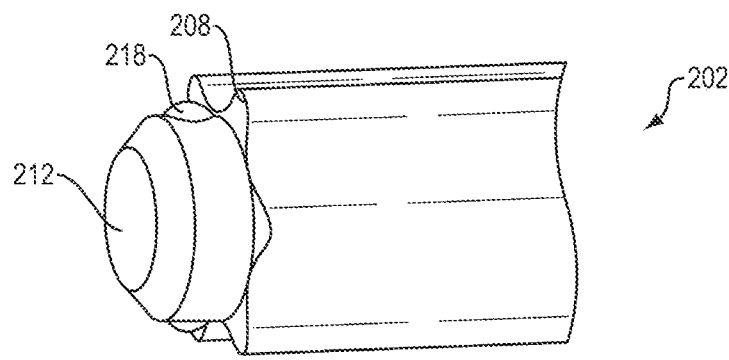
FIG. 19A is a detail view of one embodiment of a driver shaft and retention feature.
Figure 19B:
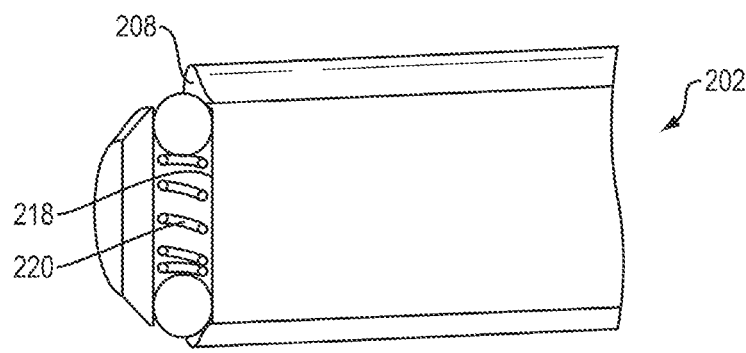
FIG. 19B is a cross-sectional detail view of the driver shaft and retention feature of FIG. 19A.
Figure 20:
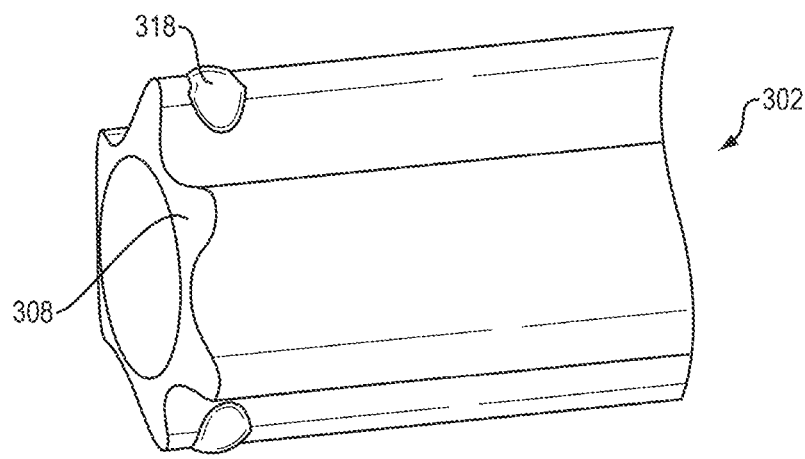
FIG. 20 is a detail view of another embodiment of a driver shaft and retention feature.
Figure 21:
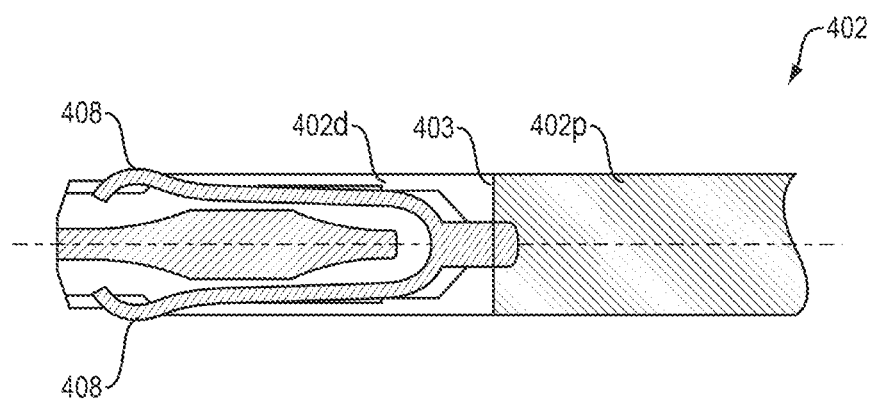
FIG. 21 is a cross-sectional side view of another embodiment of a driver shaft and retention feature.

Alternate embodiments of the drive feature formed on the distal portion of the driver shaft 108 and the retention feature 118 are shown in FIGS. 19-21. While a spring clip or circlip is discussed above, other embodiments are possible. As shown in these figures, the retention feature 218 can include a opposed ball detents that extend transversely from the distal tip of the driver shaft 202. The opposed ball detents can be biased by a spring 220 or another biasing element. The driver shaft 202 can include a protruding distal tip 212 at the distal end of a drive feature 208, as shown in FIGS. 19A and 19B. The protruding distal tip 212 can have a cylindrical profile, a diameter substantially the same as or less than a minor diameter of the drive feature 208, and can include chamfered or tapered edges to help facilitate insertion of the driver shaft and set screw disposed thereabout into, e.g., a bone screw receiver head. In other embodiments and as shown in FIG. 20, the driver shaft 302 can include a drive feature 308 that extends to the distal tip of the driver shaft and a retention feature 318 can be incorporated into the drive feature without a protruding distal tip having a different profile from the drive feature.

Figure 22:
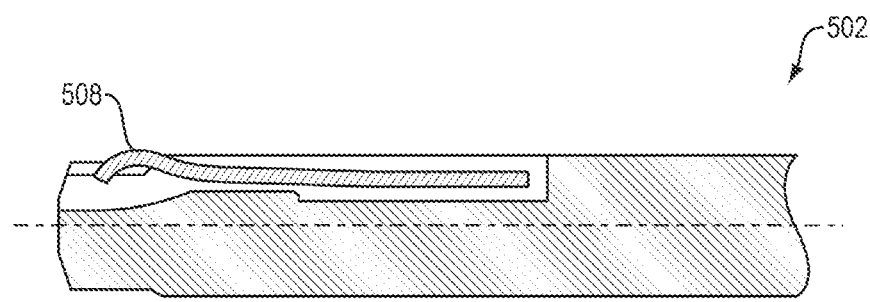
FIG. 22 is a cross-sectional side view of another embodiment of a driver shaft and retention feature.

FIGS. 21 and 22 illustrate another embodiment of a retention feature 408 that can be incorporated into a driver shaft 402. The retention feature 408 can include a leaf spring or other resilient element disposed within a recess formed in the driver shaft 402. In the embodiment of FIG. 21, the spring 408 resembles a wishbone or U-shape with a proximal end anchored within the shaft 402 and distal ends that protrude through opposed openings formed in the outer surface of the shaft. The protruding distal ends of the leaf spring 408 can be configured to retain set screws to the driver shaft via an interference fit, similar to the other retention feature embodiments described above. FIG. 22 illustrates an embodiment wherein a more linear spring element 508 provides a single protrusion from a single opening formed on the outer surface of the shaft 502. In embodiments where a resilient element is anchored within a driver shaft, the shaft can be provided in two pieces, e.g., a distal piece 402d and a proximal piece 402p shown in FIG. 21, such that the resilient element 408 can be positioned within recesses formed in each piece and the pieces can subsequently be coupled, e.g., at joint 403 by adhesive, welding, mechanical fastening, etc. Any of the above-described drive feature and retention feature embodiments can be utilized with any of the embodiments of a multiple set screw insertion instrument disclosed herein.]

In addition, the various other components of the multiple set screw inserter instrument can be configured to provide different interactions with the retention features utilized to hold a set screw against inadvertent ejection from the instrument. For example, in some embodiments the device can be configured to position a set screw just proximally of a retention feature such that a distal-facing surface of the distal-most set screw abuts a portion of the retention feature. In other embodiments, however, the instrument can be configured such that a distal-most set screw is disposed over the retention feature, such that a radially-inner-facing surface of the set screw abuts a radially-outer-facing portion of the retention feature. The different configurations can be accomplished by tuning one or more of the lengths of the outer sleeve, inner shaft, ratchet portion, and first button to achieve desired spacing and advancement. Electing to use one configuration or another can produce different tactile feedback for a user. For example, in an embodiment where the distal-most set screw stacks proximally of the retention feature, a user might feel or overcome one resistance during actuation of the first button, i.e., as the distal-most set screw is advanced over the retention feature (first resistance) and a next set screw is advanced just to abut the retention feature. In another embodiment where the distal-most set screw is positioned over the retention feature, a user might feel or overcome two resistances during actuation of the first button, i.e., as distal-most set screw is ejected off the retention feature (first resistance) and a next set screw is advanced over top of the retention feature (second resistance). Any of the various embodiments disclosed herein can be configured to operate in either manner.

Figure 23:
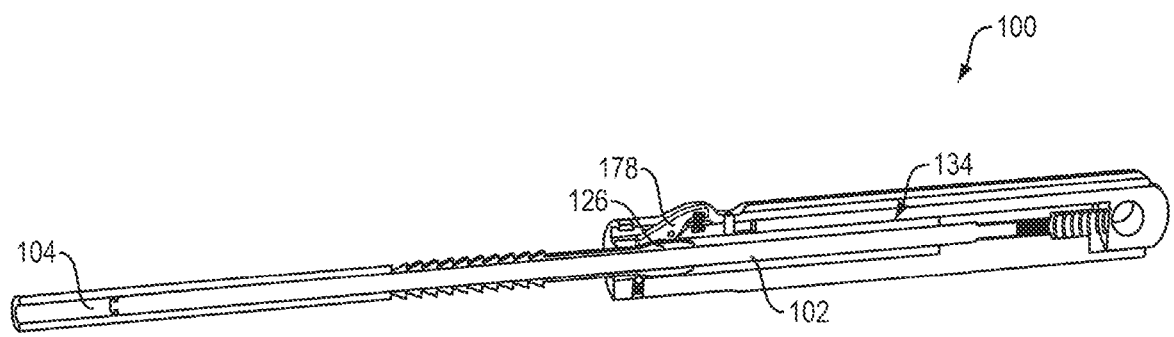
FIG. 23 is a cross-sectional perspective view of the multiple set screw insertion instrument of FIG. 1 in an expended configuration.

As noted above, the outer sleeve 104 can include the proximal head 126 that can function as a retention mechanism against inadvertent separation of the outer sleeve 104 from the device after ejection of all set screws. FIG. 23 illustrates the proximal head 126 being used to prevent the outer shaft 104 from falling distally out of the central lumen 134 and off the inner shaft 102. By way of further explanation, once the pawl or second button 178 is no longer engaged with the ratchet portion 128 of the outer sleeve 104, distal advancement of the outer sleeve can continue substantially uninterrupted until the pawl 178 engages the proximal head 126, which can have an outer diameter that is substantially the same as the outer or major diameter of the ratchet portion 128 in some embodiments. Friction between the engagement surface 180 at the distal end 178d of the pawl and the proximal head 126 can prevent separation of the outer sleeve 104 from the central lumen 134. In order to separate the outer sleeve 104 from the remainder of the instrument, a user can depress the proximal end 178p of the pawl or second button 178 to withdraw the distal end 178d radially outward and provide clearance for the proximal head 126 to pass distally out of the lumen 134 of the handle 106. In some embodiments, the proximal head 126 can include a distal-facing surface having a tapered diameter to provide a lead-in which can allow a user to remove the outer sleeve 104 by application of sufficient force without separately depressing the second button 178.

Figure 24:
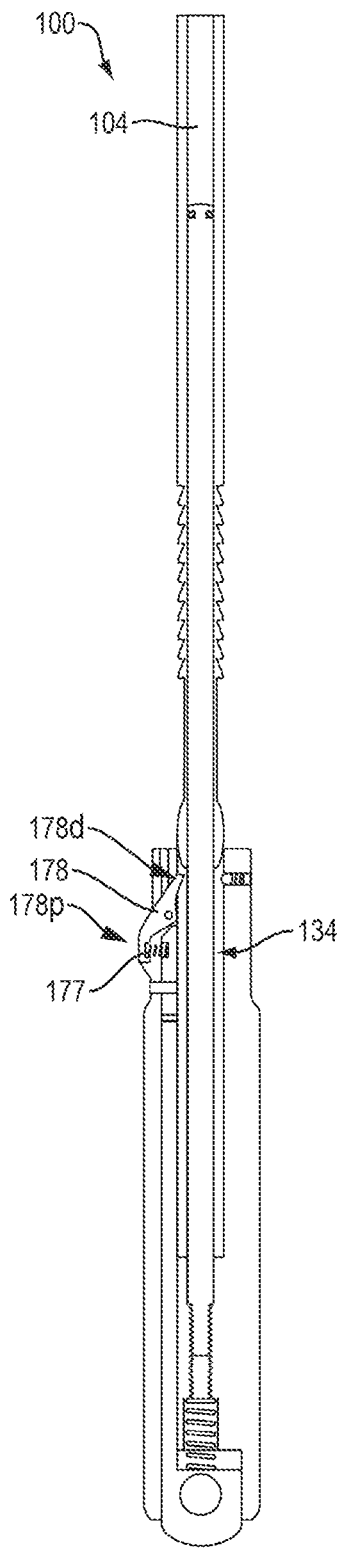
FIG. 24 is a cross-sectional side view of the multiple set screw insertion instrument of FIG. 1 having the outer shaft ejected therefrom.
Figure 25:
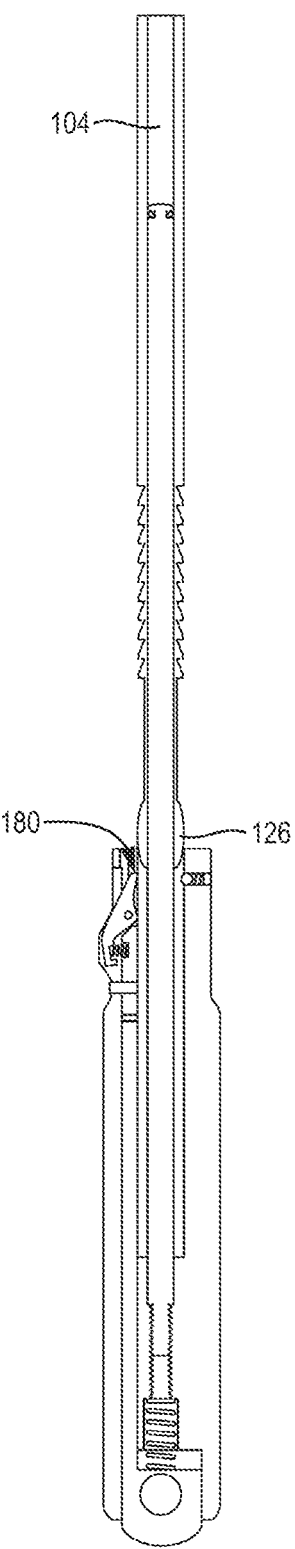
FIG. 25 is a cross-sectional side view of the multiple set screw insertion instrument of FIG. 1 with the outer shaft being inserted into the handle.
Figure 26:
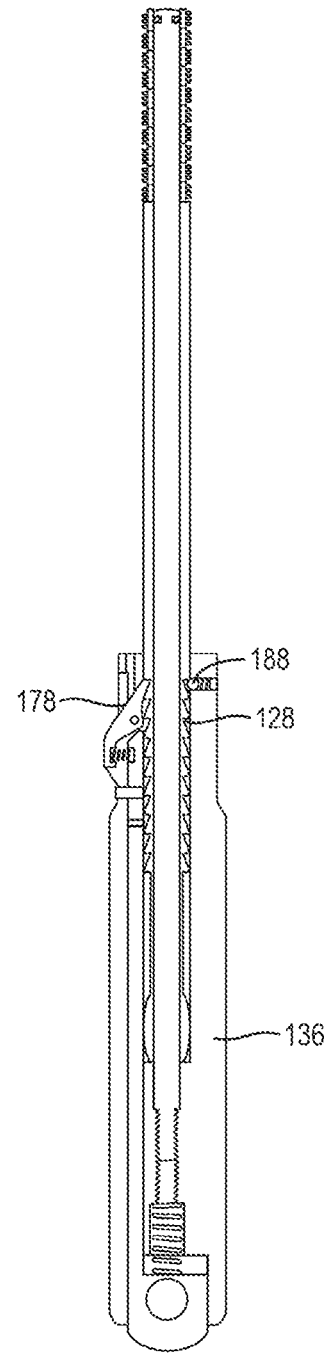
FIG. 26 is a cross-sectional side view of the multiple set screw insertion instrument of FIG. 1 reloaded into the first position.

FIGS. 24-26 illustrate the process of at least partially assembling the instrument and loading set screws. In FIG. 24, the outer sleeve 104 is shown being assembled to the remainder of the instrument 100. The outer sleeve 104 can be inserted over the driver shaft 102 proximally and, upon entering the lumen 134 of the handle 106, its distal end can abut the distal end 178d of the pawl or second button 178. In some embodiments, the proximal end 178p of the pawl or second button 178 can be pressed to compress the spring 177, pivot the distal end 178d radially outward, and allow the outer sleeve 104 to be inserted farther into the central lumen 134, as shown in FIG. 25. In some embodiments, a proximal end of the outer sleeve 104 and head 126 formed thereon can include a proximal-facing surface having a tapered diameter to provide a lead-in which can allow a user to insert the outer sleeve 104 by application of sufficient force without separately depressing the second button 178. Once the outer sleeve 104 is inserted into the handle 106 sufficiently to clear the proximal head 126 past the pawl or second button 178, it can continue until the ratchet portion 128 reaches the pawl. The proximal end 178p of the pawl or second button 178 can then be depressed to allow the outer sleeve to continue moving proximally until the pawl reaches the distal end of the ratchet portion. At this point, the distal end of the driver shaft 102 will be exposed beyond a distal end of the outer sleeve 104 and a plurality of set screws can be inserted over the distal end of the driver shaft and stacked along the drive feature 108, as shown in FIG. 26.

Figure 27:
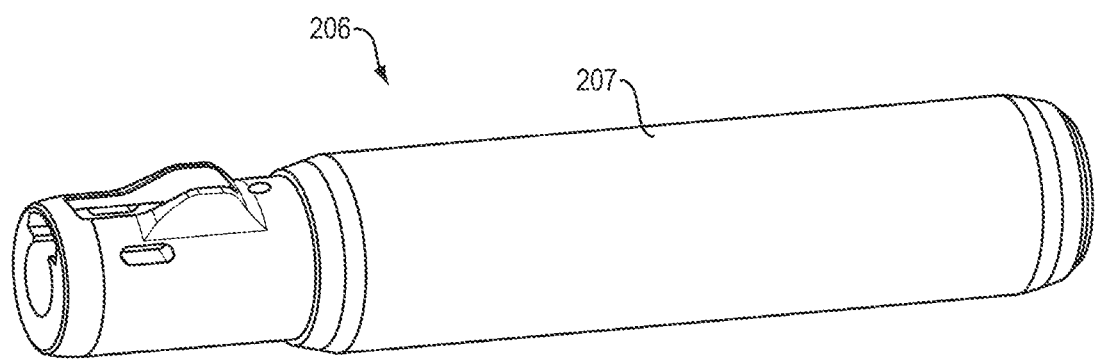
FIG. 27 is a perspective view of another embodiment of a handle according to the present disclosure.

Additional details and alternate embodiments of the instrument are shown in FIGS. 27-48. FIG. 27, for example, illustrates a handle 206 that can include a silicone overmolded grip 207. Any of a variety of materials can be utilized to form the handle, including metals, polymers, etc. Grip-enhancing features such as ribs, knurling, other texturing, etc., can be provided on an outer surface of the handle.

Figure 28:
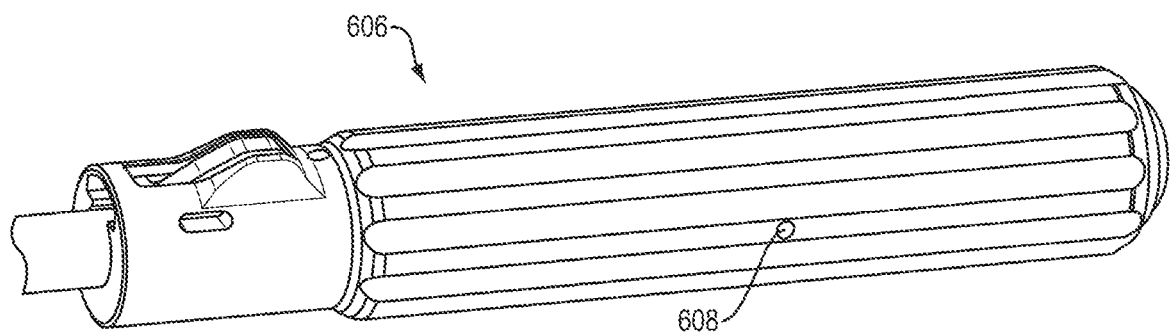
FIG. 28 is a detail view of another embodiment of a multiple set screw insertion instrument having a pin inserted through the handle.
Figure 29:
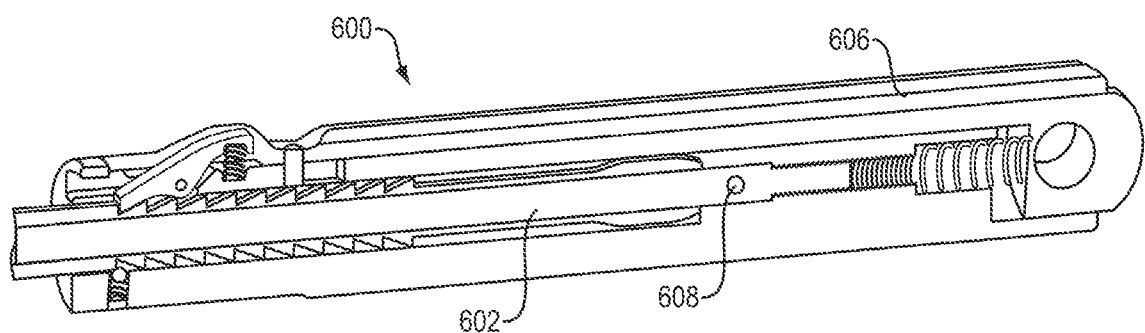
FIG. 29 is a cross-sectional detail view of the multiple set screw insertion instrument of FIG. 28.
Figure 30:
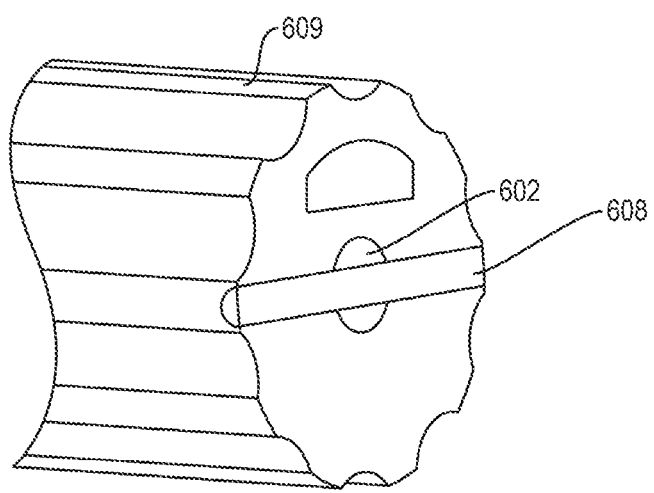
FIG. 30 is a cross-sectional detail view of the pin passing through the multiple set screw insertion instrument of FIG. 28.

FIGS. 28-30 illustrate an embodiment wherein a handle 606 includes a bore formed therein to receive a pin 608 that can help secure a driver shaft 602 to the handle. As shown, the pin 608 can extend transversely through the handle 606 of the inserter instrument 600 and through the inner driver shaft 602 to prevent unwanted rotation of the driver shaft relative to the handle during use. In embodiments where the driver shaft 602 is threadably coupled to the handle 606, undesired relative rotation between these components during use could cause separation or adjustment of relative positioning. The use of pin 608 disposed through coaxial transverse bores formed in the handle 606 and the shaft 602 can prevent any such relative rotation between these components.

Figure 31:
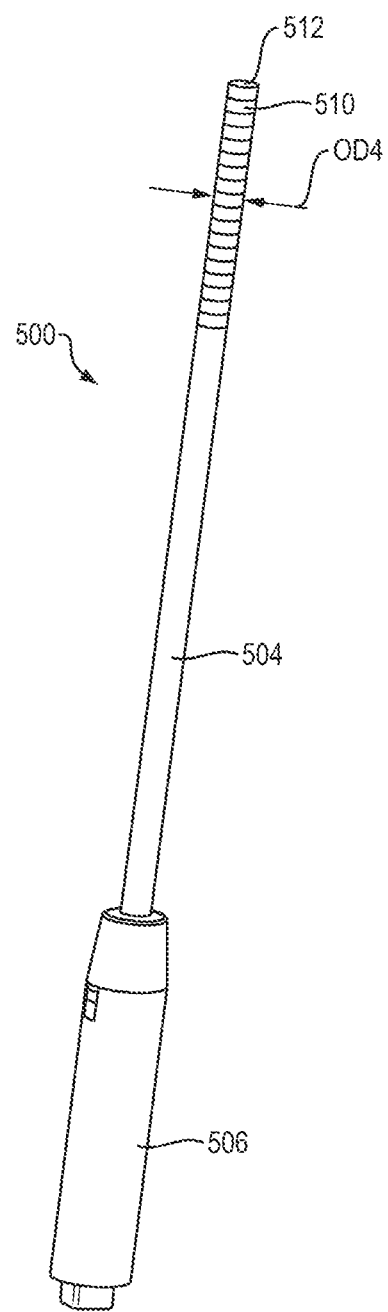
FIG. 31 is a perspective view of another embodiment of a multiple set screw insertion instrument.

FIG. 31 illustrates another embodiment of a multiple set screw insertion instrument 500. The overall profile of the instrument 500 can be similar to an intermediate set screw driver. The inserter 500 can include an inner driver shaft 502 with a relatively long male drive feature on the distal end and a spring clip retention mechanism at the distal tip 512. A number of set screws 510 with a female drive feature cut completely through them can be stacked on the driver along its axis. Stacking the set screws 510 in this way can allow the diameter of the instrument 500 at the distal end to remain no larger than the outer diameter OD4 of the set screw, facilitating instrument compatibility without increasing instrument profile. A ratcheting outer sleeve 504 can advance over the inner driver shaft 502, moving the next set screw to the retention feature at the distal tip 512 of the driver after insertion of the previous set screw. The ratcheting feature can provide a hard stop behind the set screw which can aid a user in starting to thread into the implant. A proximal handle 506 can have a diameter small enough to limit the amount of torque applied by a user and can contain two buttons. A first button at the proximal end can be pressed to advance the outer sleeve 504 and set screws 510. The second, on the side of the handle 506, can be pressed to return the outer sleeve 504 proximally and reload the instrument. A retention mechanism on the handle can temporarily hold the outer sleeve in place when the proximal button is released to allow the ratchet mechanism to advance.

Figure 32:
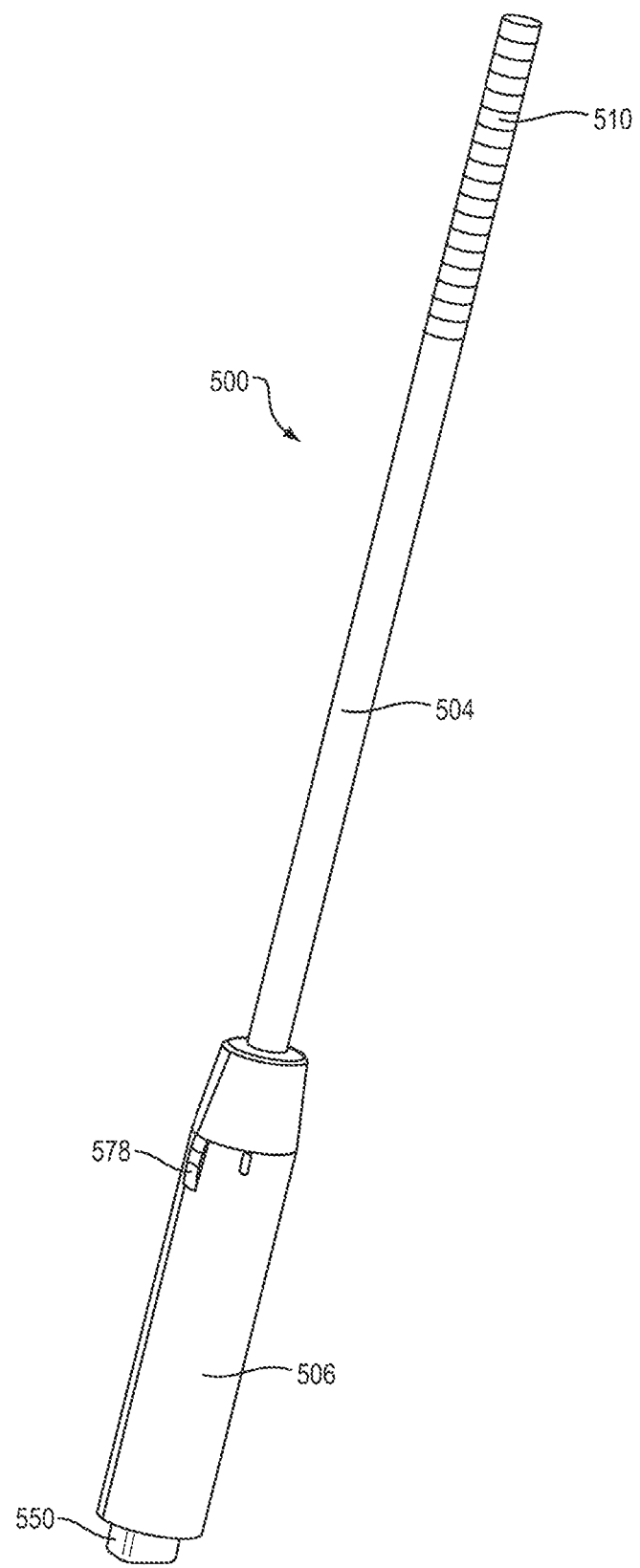
FIG. 32 is perspective view of the multiple set screw insertion instrument of FIG. 31.

FIG. 32 illustrates an alternative view of the multiple set screw insertion instrument 500. As noted above, the instrument 500 can reduce time and passes required to install several set screws when assembling a spinal fixation construct, savings that can be significant in long deformity correction cases where the construct spans several vertebral levels and includes several termination or fixation points between a rod or other spinal fixation element and implanted bone anchors. The relatively low profile cylindrical handle 506 can discourage the application of large amounts of torque to the set screws, and the reduced diameter distal portion can allow for set screw delivery through instrumentation, such as extension tubes coupled to the implanted bone anchors, etc.

The above-described features of the inserter are shown in FIG. 32 as well, including the button 550 on the proximal end that controls advancing the ratcheting outer sleeve 504 over the inner sleeve to push the loaded set screws 510 distally and ready a second set screw after delivery of a first set screw. Also shown is the second button 578 on the side of the handle 506 that allows for proximal movement of the outer sleeve 504 to reload the device with additional set screws. Finally, the figure shows a plurality of set screws 510 stacked over the inner shaft at the distal end of the inserter 500.

Figure 33:
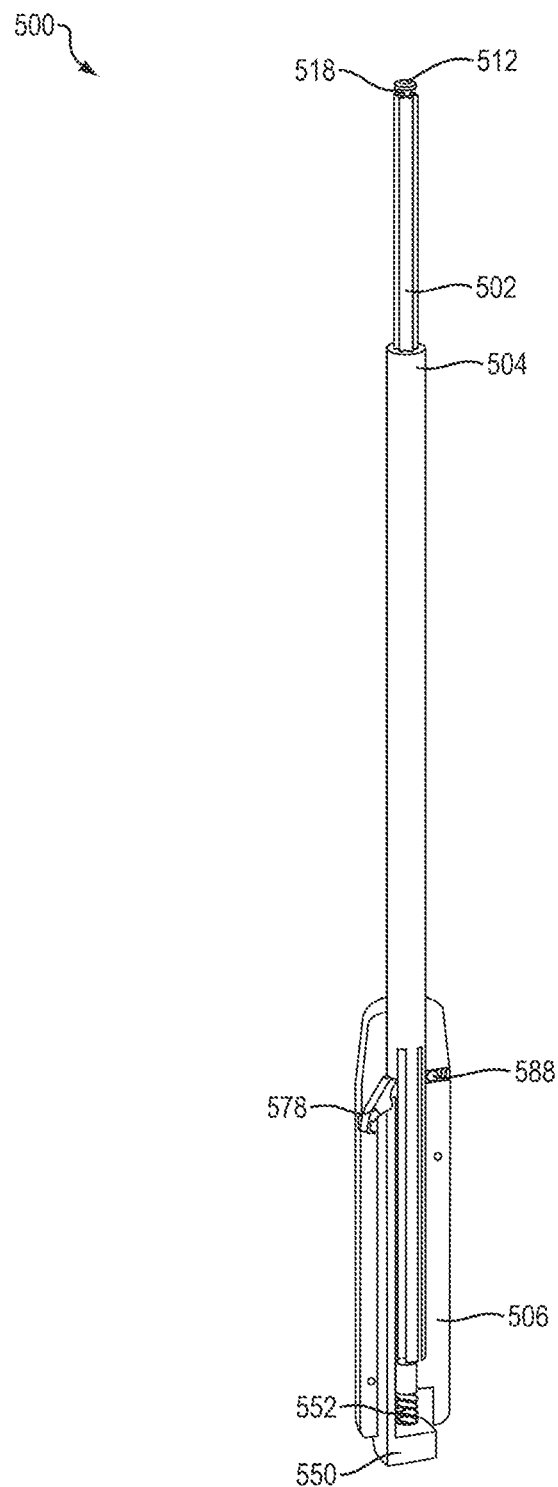
FIG. 33 is a cross-sectional view of the multiple set screw insertion instrument of FIG. 31.
Figure 34:
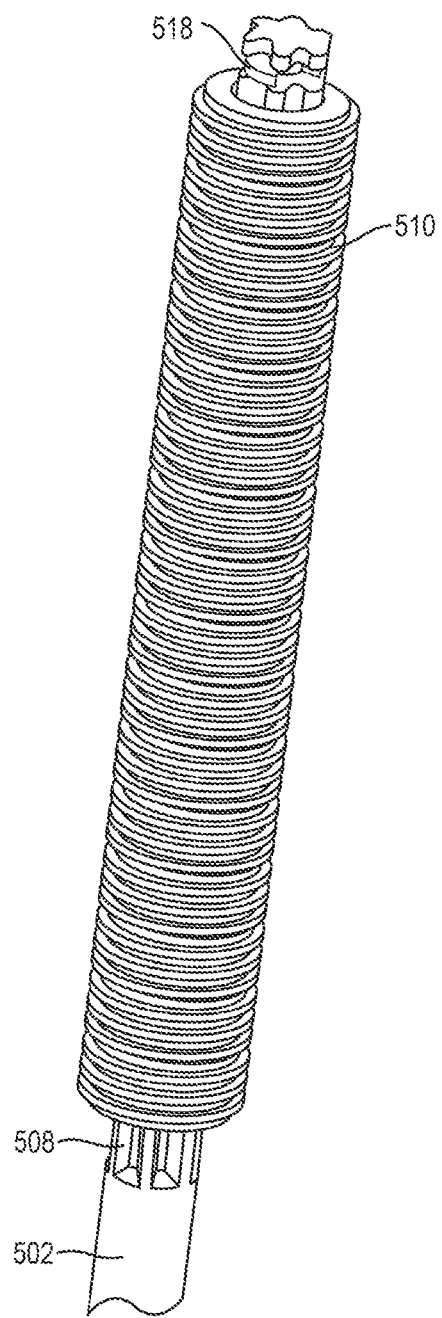
FIG. 34 is a perspective view of the driver shaft of the multiple set screw insertion instrument of FIG. 31.

FIG. 33 shows a partially-transparent view of the inserter 500 of FIG. 32 to illustrate its operation and internal mechanics in greater detail. Starting at the distal end of the device, the inner shaft 502 includes an extended distal portion having a driver tip 512 geometry to allow stacking multiple set screws over the tip. As shown in FIG. 34, there is a spring clip 518 disposed at a distal end of the driver to provide soft set screw retention due to interference between the spring clip 518 and set screw 510. At the proximal end, a spring or other bias element 552 urges the button 550 proximally to return it after a user presses the button to advance the outer sleeve 504. The proximal button 550 interfaces with the side button 578 to transfer the load from the proximal button 550 to the outer sleeve 504. A spring plunger 588 prevents the ratcheting outer sleeve 504 from following the side button 578 during its return stroke with the proximal button 550.

Figures 35A, 35B, 35C, 35D:
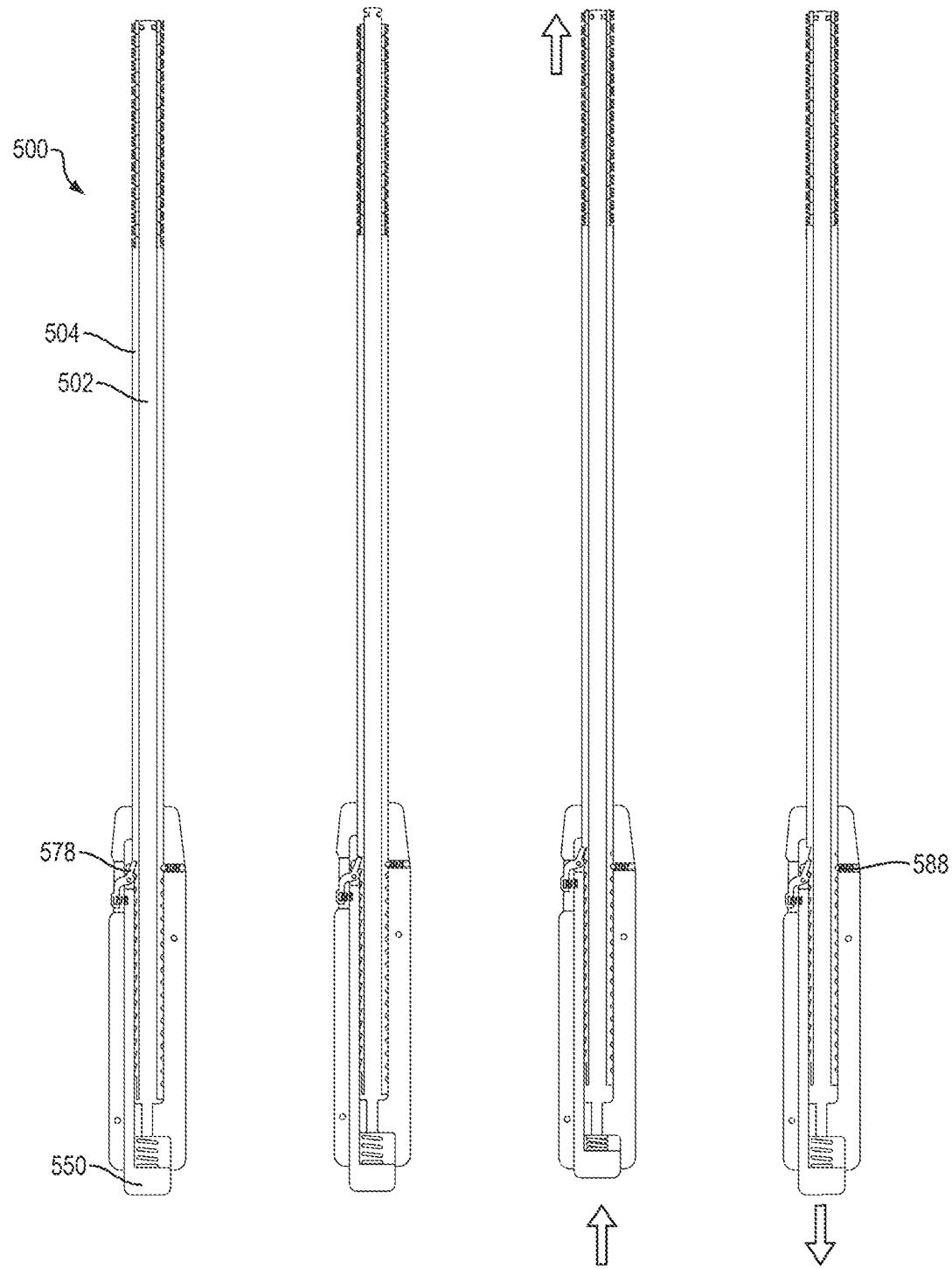
FIG. 35A is a cross-sectional side view of the multiple set screw insertion instrument of FIG. 31 in a first position.
FIG. 35B is a cross-sectional side view of the multiple set screw insertion instrument of FIG. 31 following set screw insertion.
FIG. 35C is a cross-sectional side view of the multiple set screw insertion instrument of FIG. 31 in a second position with a button depressed to advance the outer sleeve.
FIG. 35D is a cross-sectional side view of the multiple set screw insertion instrument of FIG. 31 in a third position that is reset for set screw insertion.

FIGS. 35A-35D illustrate the set screw insertion process in cross-sectional views. A user first inserts the distal-most set screw into a receiver head or tulip of an implanted bone anchor. The user then rotates the inserter 500 to thread the set screw into the threaded portion of the bone anchor receiver head. The user then pulls the inserter proximally to separate it from the implanted set screw. The force of the user's pull and the secure threaded position of the set screw in the receiver head causes the set screw to overcome the distal spring clip and separate from the inserter, as shown in FIG. 35B. The user can then press the proximal button 550 to advance the side button 578 and the outer ratcheting sleeve 504 relative to the inner shaft 502 and urge the stacked set screws distally until the distal-most set screw approaches the distal end of the inserter 500 and stops due to interference with the spring clip, as shown in FIG. 35C. As the ratcheting outer sleeve 504 advances distally, a spring plunger 588 indexes from a first detent to an adjacent detent on the outer sleeve 504. The spring plunger 588 provides enough retention force to temporarily maintain the position of the outer sleeve 504 when the proximal button 440 is released and travels with the side button 578 back to the initial position where they can be advanced again after delivery of another set screw, as shown in FIG. 35D.

Figure 36A:
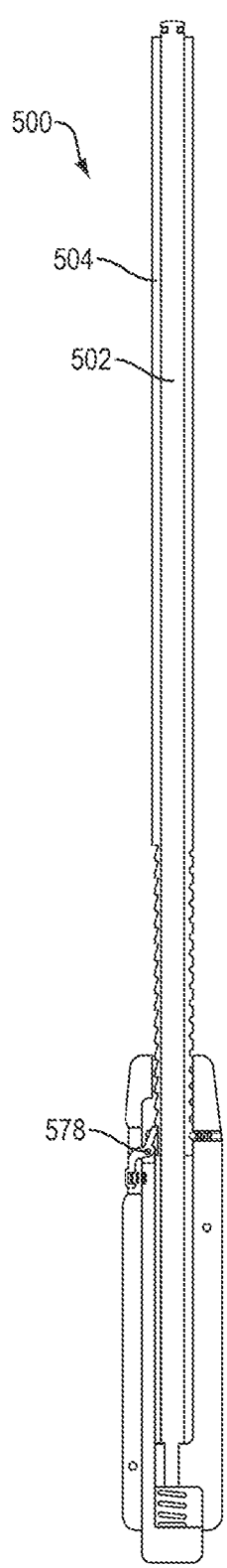
FIG. 36A is a cross-sectional side view of the multiple set screw insertion instrument of FIG. 31 in a fourth position having the outer shaft ejected therefrom.
Figure 36B:
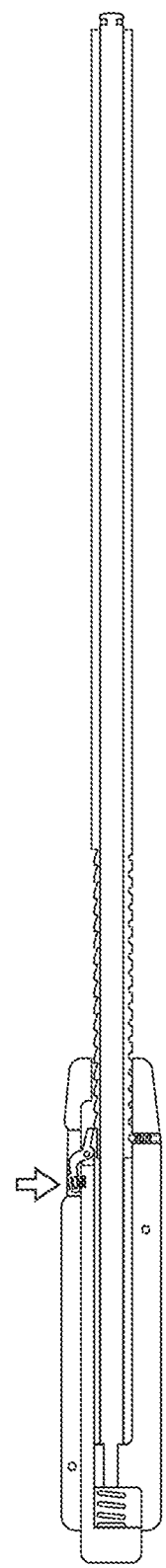
FIG. 36B is a cross-sectional side view of the multiple set screw insertion instrument of FIG. 31 in a fifth position with the outer shaft being reintroduced into the handle.
Figure 36C:
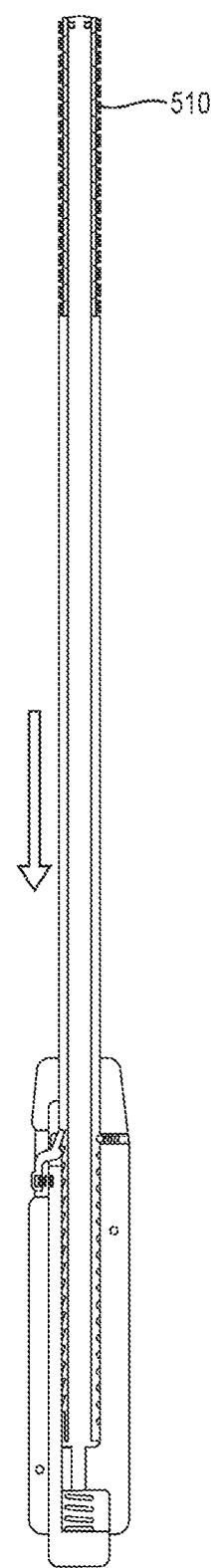
FIG. 36C is a cross-sectional side view of the multiple set screw insertion instrument of FIG. 31 reloaded into the first position.

FIGS. 36A-36C illustrate the set screw reloading process in cross-sectional views. As shown in FIG. 36A, the ratcheting outer sleeve 504 can be in a distal-most position after all set screws have been delivered. To reload, a user can press and hold down the recessed side button 578, as shown in FIG. 36B, which can release the ratcheting outer sleeve 504 to move proximally when sufficient force is applied to overcome the spring plunger retention force, as shown in FIG. 36C. Additional set screws 510 can then be loaded onto the distal drive tip portion and stacked together, as shown in FIG. 36C. Once the recessed side button 578 is released, it will again interface with one of the ratchet teeth of the outer sleeve 504 to maintain its position and control advancement of the outer sleeve 504 when the proximal button is depressed.

Figure 37:
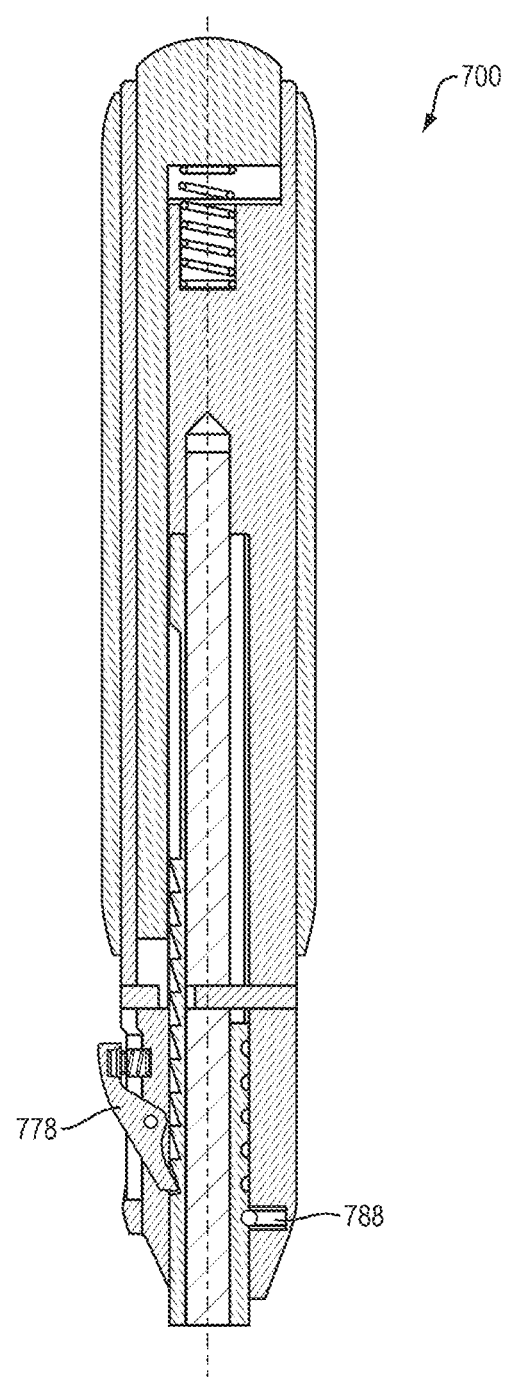
FIG. 37 is a cross-sectional detail view of an embodiment of a multiple set screw insertion instrument handle.
Figure 38:
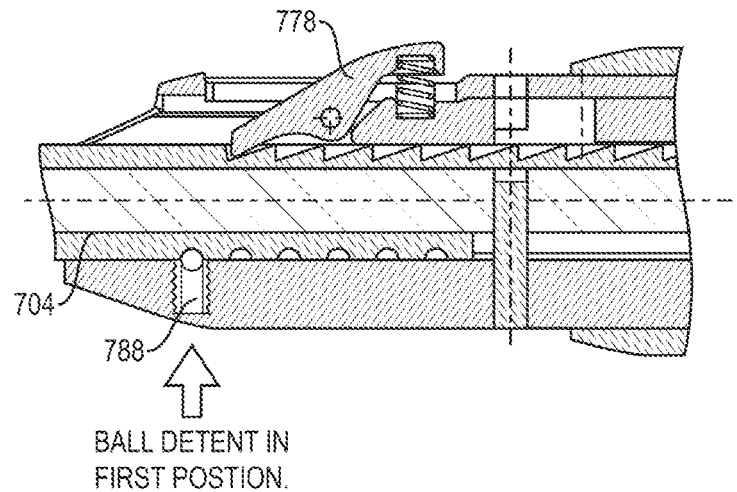
FIG. 38 is a cross-sectional detail view of the multiple set screw insertion instrument of FIG. 37 in a first positon.
Figure 39:
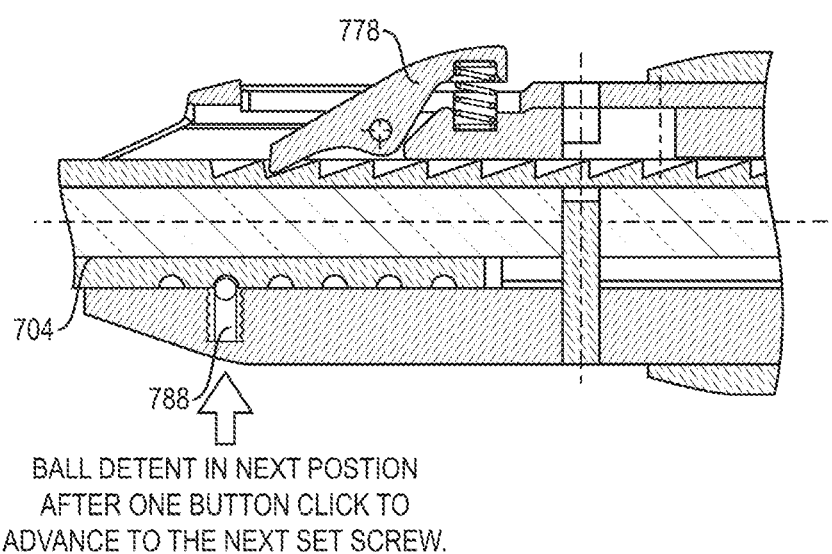
FIG. 39 is a cross-sectional detail view of the multiple set screw insertion instrument of FIG. 37 in a second position.
Figures 40A, 40B, 40C, 40E:
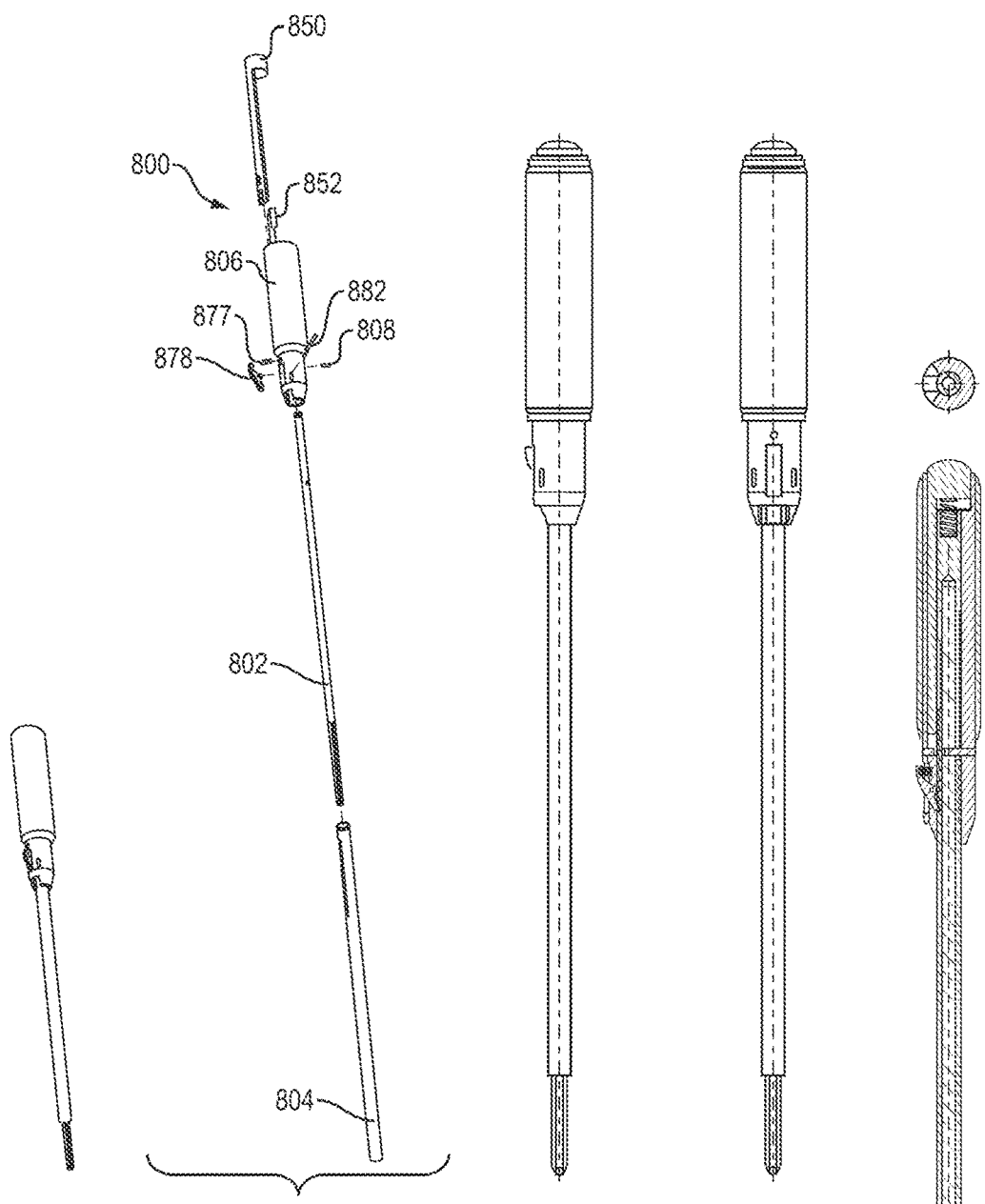
FIG. 40A is a perspective view of one embodiment of a multiple set screw insertion instrument.
FIG. 40B is an exploded perspective view of the multiple set screw insertion instrument of FIG. 40A.
FIG. 40C is a side view of the multiple set screw insertion instrument of FIG. 40A.
FIG. 40E is a top view of the multiple set screw insertion instrument of FIG. 40A.
Figure 40D:
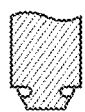
FIG. 40D is a cross-sectional detail view of the distal end of the multiple set screw insertion instrument of FIG. 40A.
Figure 40F:
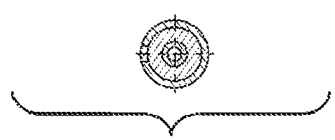
FIG. 40F is a cross-sectional side view of the multiple set screw insertion instrument of FIG. 40A.
Figures 41A, 41B, 41C, 41D:
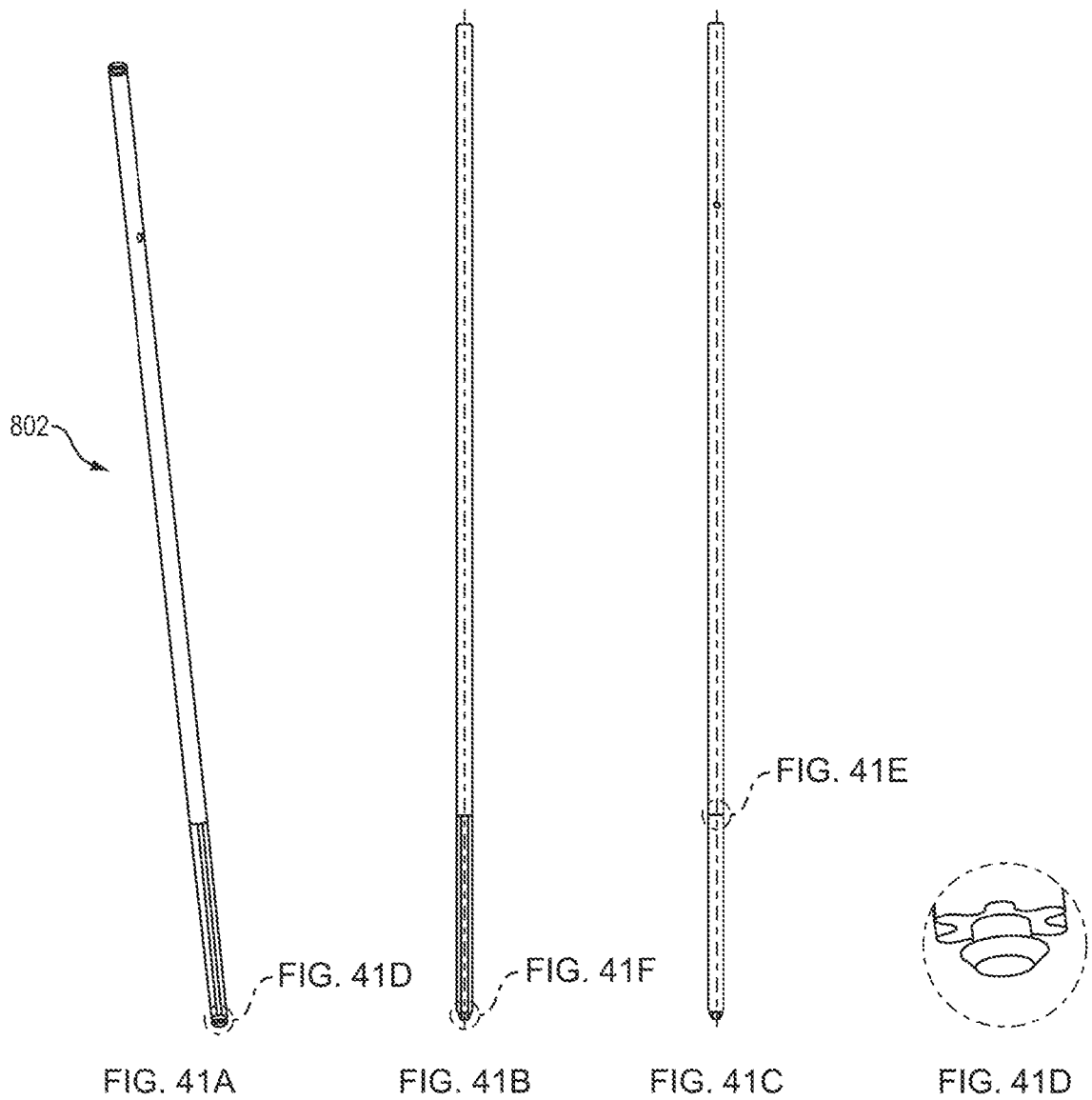
FIGS. 41A-41G illustrate the set screw inserter shaft of the instrument of FIG. 40A.
Figures 41E, 41F, 41G:
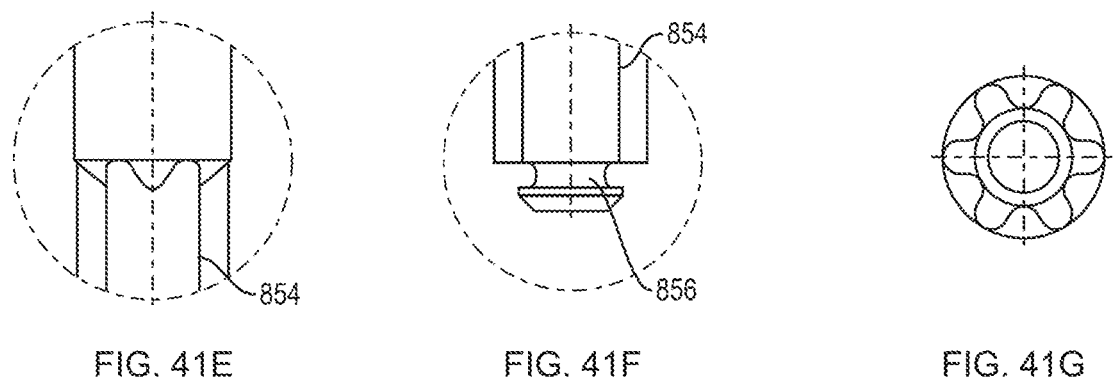
Figure 42A:
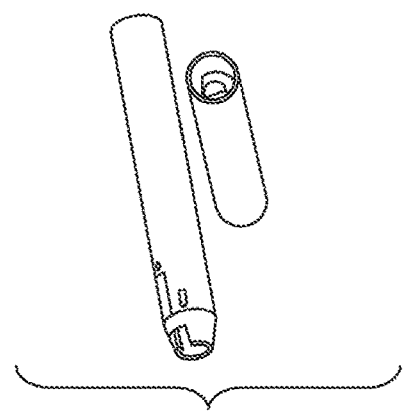
FIGS. 42A-42D illustrate the set screw inserter handle of the instrument of FIG. 40A.
Figure 42B:
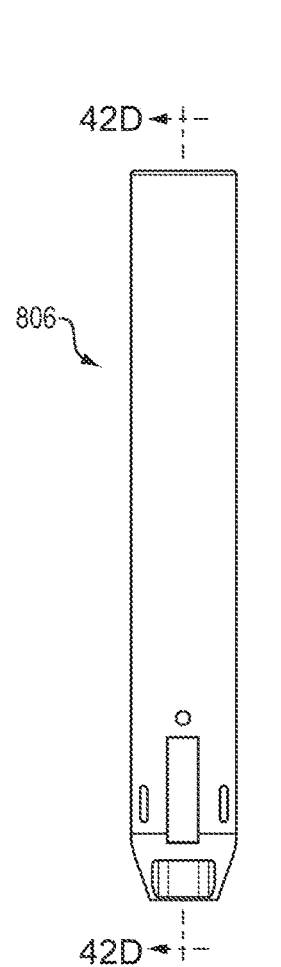
Figure 42C:
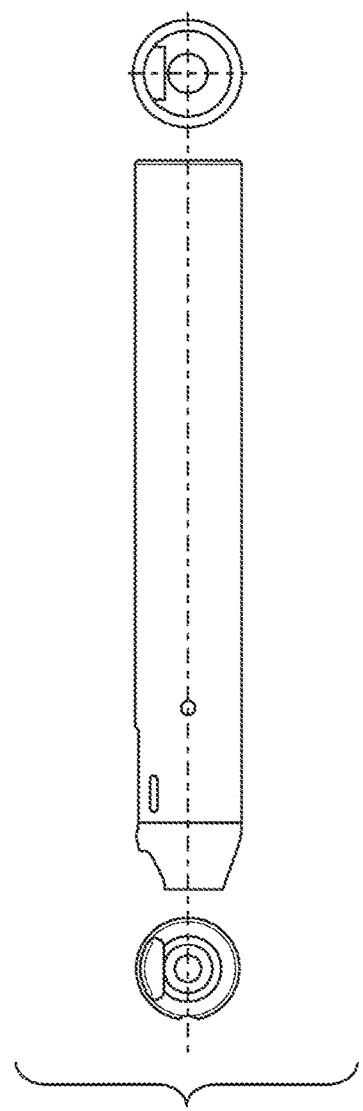
Figure 42D:
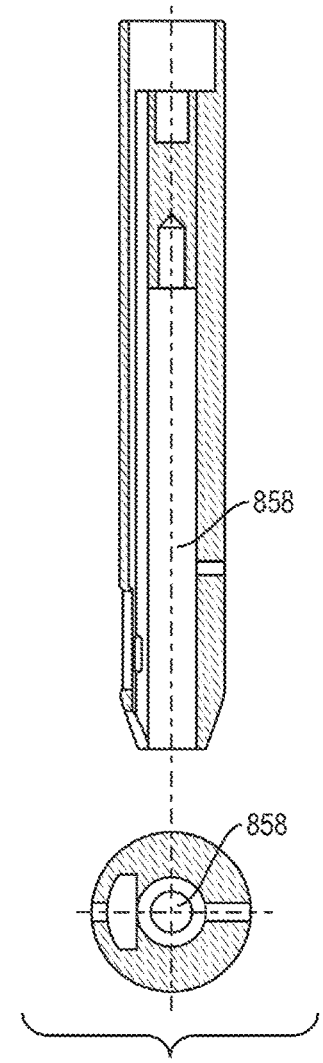

FIGS. 37-39 illustrate a cross-sectional view of another embodiment 700 with a side button or latch 778 that extends outside the handle. In particular, FIGS. 38 and 39 illustrate the relative positions of a spring plunger/ball detent 788 when the outer sleeve 704 is in a first position and after the outer sleeve 704 has been advanced to deliver a new set screw.

FIGS. 40A-48 illustrate additional views of embodiments of a multiple set screw insertion instrument. More particularly, FIGS. 40A-40F illustrate various views of one embodiment of a multiple set screw insertion instrument 800, including an exploded view showing outer sleeve 804, inserter shaft 802, handle 806, dowel 808 for securing the inserter shaft 802 to the handle 806, side latch 878, bias spring 877 and pivot pin 882 for side latch 878, proximal actuator button 850, and bias spring 852 for actuator button.

FIGS. 41A-41G illustrate various views of a set screw inserter shaft 802, including its distal portion with drive tip geometry 854 and groove 856 to receive a spring clip.

FIGS. 42A-42D illustrate various views of a set screw inserter handle 806, including a lumen 858 to receive the inserter shaft, ratcheting outer sleeve, proximal button, and side latch components.

Figure 43A:
FIGS. 43A-43C illustrate the actuator button of the instrument of FIG. 40A.
Figure 43B:
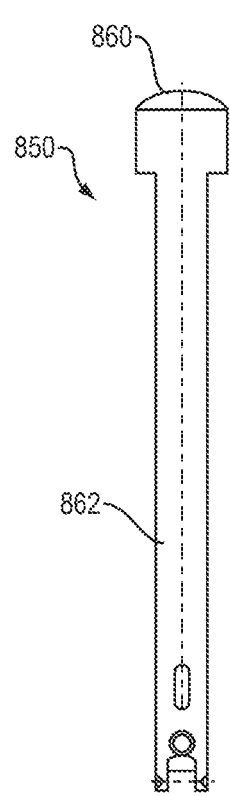
Figure 43C:
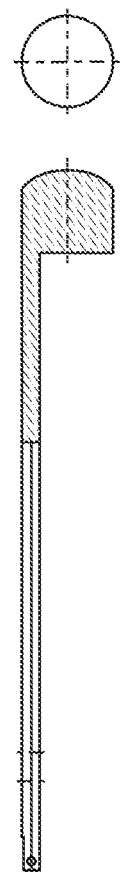
Figure 44A:
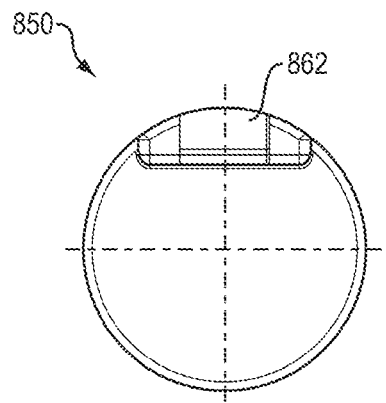
FIGS. 44A-44C illustrate the distal end of the actuator button of FIG. 43A.
Figure 44B:
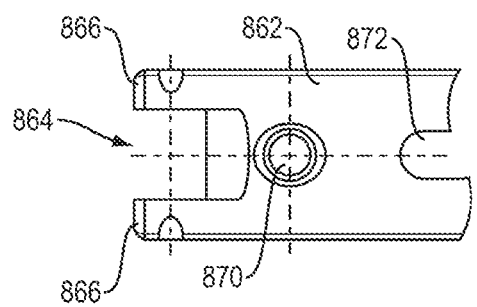
Figure 44C:
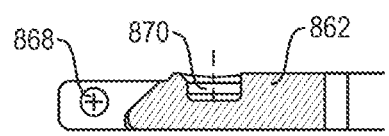
Figure 45A:
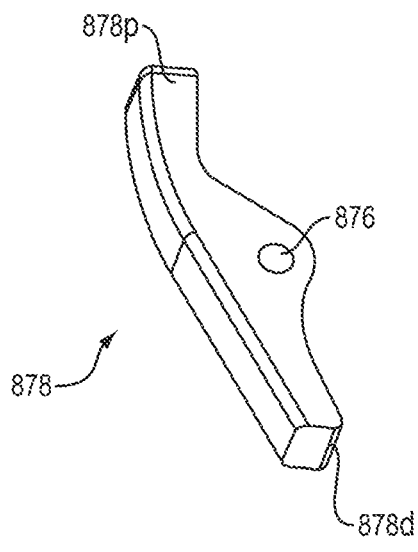
FIGS. 45A-45E illustrate the side latch of the instrument of FIG. 40A.
Figure 45B:
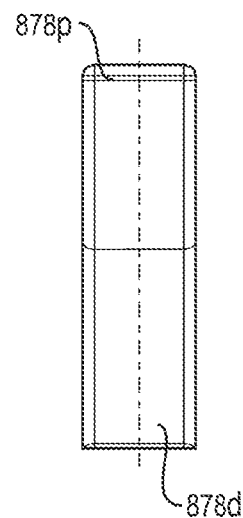
Figure 45C:
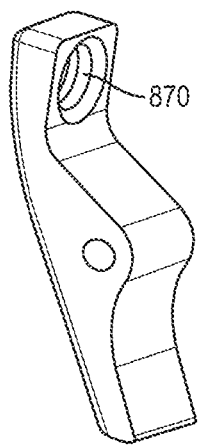
Figure 45D:
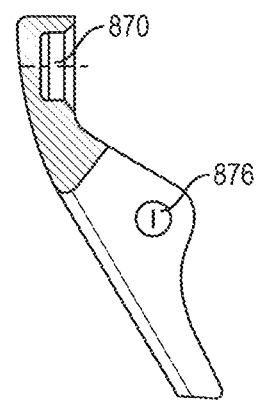
Figure 45E:
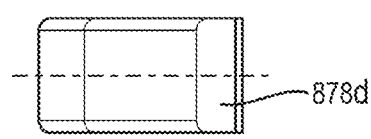

FIGS. 43A-43C illustrate various views of an actuator button 850, including the proximal button surface 860 contacted by a user and a distally-extending portion 862 that interfaces with the side latch or second button 878. FIGS. 44A-44C illustrate various detail views of the distal end of the actuator button 850 that interfaces with the side latch, including a cutout 864 with protruding flanges 866 having bores 868 formed therein that can receive the pin 882 to couple the side latch or second button 878 to the distally-extending portion 862. Also shown is a recess 870 that can receive the bias spring 877 and part of the slot 872 that can receive the dowel 808 to limit the range of motion of the button 850 relative to the handle 806.

FIGS. 45A-45E illustrate various views of the side latch 878, including its proximal end 878*p* having a recess 874 to receive the bias spring 877, its distal end 878*d*, and bore 876 that receives pin 882.

Figure 46A:
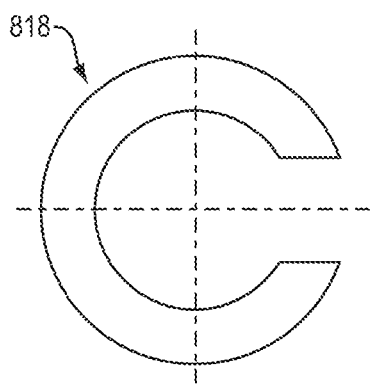
FIGS. 46A-46C illustrate the spring clip of the instrument of FIG. 40A.
Figure 46B:
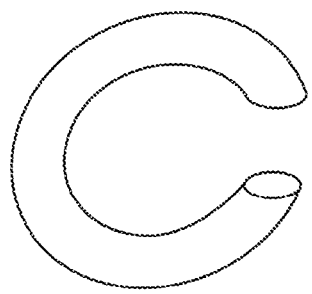
Figure 46C:
Figures 47A, 47B, 47C, 47D:
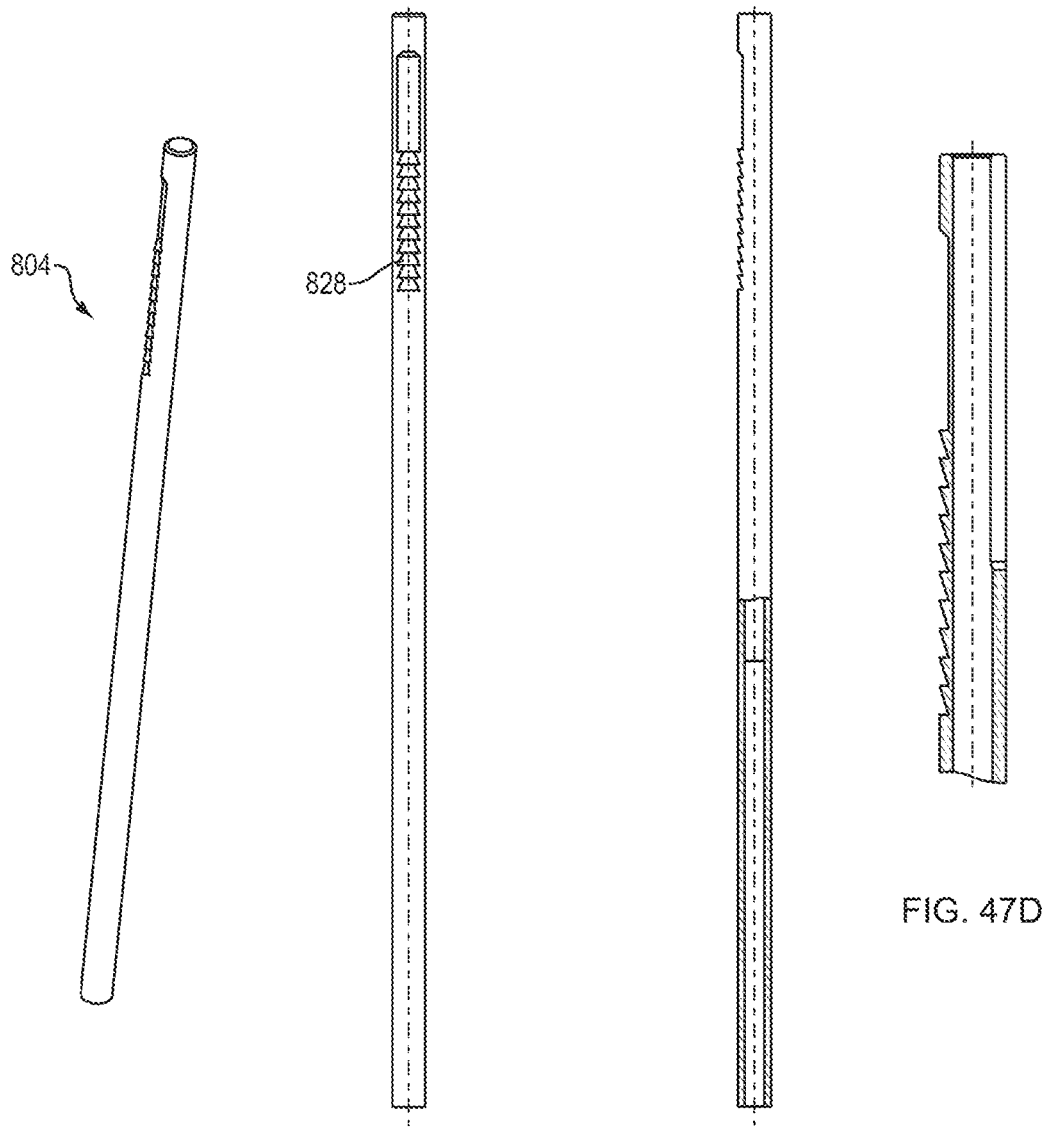
FIGS. 47A-47D illustrate the outer ratcheting sleeve of the instrument of FIG. 40A.

FIG. 46A-46C illustrate various views of the spring clip 818 that retains set screws on the inserter shaft by interference fit.

FIG. 47A-47D illustrate various views of the outer ratcheting sleeve 804, including a proximal portion with ratchet teeth 828 that interface with the side latch 878. Note that in this embodiment the ratchet teeth 828 are formed over only a portion of an outer circumference of the sleeve 804. In other embodiments, as disclosed above, the ratchet teeth 828 can be formed around an entire circumference of the outer sleeve 804. Further, in some embodiments a first set of ratchet teeth or other surface features can be formed on one side of the outer sleeve and a second set of ratchet teeth or other surface features can be formed on another side of the outer sleeve, e.g., to provide different surface features to interact with each of the second button and the detent/spring plunger.

Figure 48:
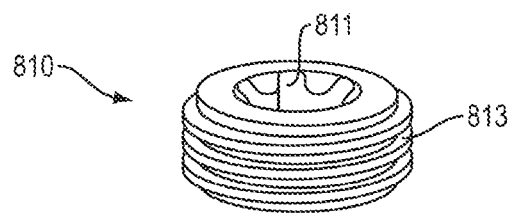
FIG. 48 illustrates one embodiment of a set screw for use with the multiple set screw insertion instrument of FIG. 40A.

FIG. 48 illustrates one embodiment of a set screw 810 for use with the multiple set screw insertion instrument 800. The set screw 810 can include a through-bore 811 formed therein with a geometry complementary to the inserter shaft distal portion 854 to allow the set screw to stack onto the inserter shaft 802 and be driven by the inserter shaft 802 when the inserter 800 is rotated. The set screw 810 can also include threads 813 formed on an outer surface thereof that can interface with threads formed on, e.g., an inner surface of a bone screw receiver head during insertion thereof using the instrument 800.

The instruments disclosed herein can be constructed from any of a variety of known materials. Example materials include those which are suitable for use in surgical applications, including metals such as stainless steel, titanium, nickel, cobalt-chromium, or alloys and combinations thereof, polymers such as PEEK, ceramics, carbon fiber, and so forth.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any of a variety of surgical procedures with any human or animal subject, or in non-surgical procedures.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning of a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

Further features and advantages based on the above-described embodiments are possible and within the scope of the present disclosure. Accordingly, the disclosure is not to be limited by what has been particularly shown and described. All publications and references cited herein are incorporated by reference in their entirety, except for any definitions, subject matter disclaimers or disavowals, and except to the extent that the incorporated material is inconsistent with the express disclosure herein, in which case the language in this disclosure controls.

Examples of the above-described embodiments can include the following:

1. A surgical instrument, comprising:
    a shaft with a distal portion configured to drive a set screw and seat a plurality of set screws stacked against one another on the shaft;
    a handle coupled to the shaft;
    a sleeve disposed over the shaft and configured to contact a proximal-most set screw stacked on the shaft;
    a first button disposed in the handle and configured to advance the sleeve distally relative to the shaft by a first increment; and
    a second button disposed in the handle and configured to permit retraction of the sleeve proximally.
2. The instrument of claim 1, wherein the sleeve includes a plurality of ratchet teeth.
3. The instrument of claim 2, wherein the first increment corresponds to a distance between two adjacent teeth of the plurality of ratchet teeth.
4. The instrument of claim 2, further comprising a detent disposed in the handle that is configured to interface with the plurality of ratchet teeth to resist movement of the sleeve.
5. The instrument of claim 4, wherein the detent is a spring-biased ball.
6. The instrument of claim 2, wherein the second button is biased to contact a ratchet tooth of the plurality of ratchet teeth.
7. The instrument of claim 6, wherein the second button permits proximal retraction of the sleeve when the bias of the second button is overcome.
8. The instrument of any of claims 1 to 7, further comprising a spring clip disposed around a distal end of the shaft and configured to retain a set screw thereon by interference fit.
9. The instrument of any of claims 1 to 8, wherein movement of the first button causes movement of the second button.
10. The instrument of claim 9, wherein movement of the first button translates the second button distally.

11. The instrument of claim 10, wherein the first button is biased proximally such that proximal movement of the first button moves the second button proximally relative to the sleeve.

12. The instrument of any of claims 1 to 11, wherein an outer diameter of the plurality of set screws stacked on the shaft is substantially equal to an outer diameter of the sleeve disposed over the shaft.

13. The instrument of any of claims 1 to 12, wherein the sleeve further comprises a retention mechanism thereon for preventing ejection of the sleeve from the handle.

14. The instrument of claim 13, wherein the retention mechanism abuts the second button to retain the sleeve within the handle.

15. The instrument of any of claims 1 to 14, wherein the first button is disposed on a proximal end of the handle and the second button is disposed on a side of the handle.

16. The instrument of any of claims 1 to 15, wherein the first button is biased.

17. The instrument of any of claims 1 to 16, wherein the second button is biased.

18. A surgical method, comprising:
    delivering a first set screw to a first implanted bone anchor using an inserter;
    actuating the inserter to advance a second set screw distally relative to a shaft of the inserter; and
    delivering a second set screw to a second implanted bone anchor using the inserter.

19. The method of claim 18, wherein actuating the inserter includes depressing a first button disposed in a handle of the inserter.

20. The method of any of claims 18 to 19, wherein actuating the inserter includes advancing a sleeve disposed over the shaft distally to urge the second set screw toward a distal end of the shaft.

21. A surgical method, comprising:
    actuating a first button disposed in a handle of an inserter;
    sliding a sleeve disposed over a shaft of the inserter proximally; and
    advancing a plurality of set screws proximally over a distal portion of the shaft of the inserter.

22. The method of claim 21, wherein the first button is disposed in a side of the handle.

23. The method of any of claims 21 to 22, wherein the sleeve slides to abut a proximal wall of a recess formed in the handle.

What is claimed is:

1. A surgical instrument, comprising:
    a shaft with a distal portion configured to drive a set screw and seat a plurality of set screws stacked against one another on the shaft;
    a handle coupled to the shaft;
    a sleeve disposed over the shaft and configured to contact a proximal-most set screw stacked on the shaft;
    a first button disposed in the handle and configured to advance the sleeve distally relative to the shaft by a first increment; and
    a second button disposed in the handle and configured to permit retraction of the sleeve proximally.

2. The instrument of claim 1, wherein the sleeve includes a plurality of ratchet teeth.

3. The instrument of claim 2, wherein the first increment corresponds to a distance between two adjacent teeth of the plurality of ratchet teeth.

4. The instrument of claim 2, further comprising a detent disposed in the handle that is configured to interface with the plurality of ratchet teeth to resist movement of the sleeve.

5. The instrument of claim 4, wherein the detent is a spring-biased ball.

6. The instrument of claim 2, wherein the second button is biased to contact a ratchet tooth of the plurality of ratchet teeth.

7. The instrument of claim 6, wherein the second button permits proximal retraction of the sleeve when the bias of the second button is overcome.

8. The instrument of claim 1, further comprising a spring clip disposed around a distal end of the shaft and configured to retain a set screw thereon by interference fit.

9. The instrument of claim 1, wherein movement of the first button translates the second button distally.

10. The instrument of claim 9, wherein the first button is biased proximally such that proximal movement of the first button moves the second button proximally relative to the sleeve.

11. The instrument of claim 1, wherein an outer diameter of the plurality of set screws stacked on the shaft is substantially equal to an outer diameter of the sleeve disposed over the shaft.

12. The instrument of claim 1, wherein the sleeve further comprises a retention mechanism thereon for preventing ejection of the sleeve from the handle.

13. The instrument of claim 12, wherein the retention mechanism abuts the second button to retain the sleeve within the handle.

14. The instrument of claim 1, wherein the first button is disposed on a proximal end of the handle and the second button is disposed on a side of the handle.

* * * * *